(12) United States Patent
Tian et al.

(10) Patent No.: US 11,186,599 B2
(45) Date of Patent: Nov. 30, 2021

(54) PHOSPHONAMIDE ESTER COMPOUND, SALT THEREOF, RELATED CRYSTAL FORM THEREOF, PREPARATION METHOD THEREFOR AND USE THEREOF

(71) Applicant: SICHUAN KELUN-BIOTECH BIOPHARMACEUTICAL CO., LTD., Chengdu (CN)

(72) Inventors: Qiang Tian, Chengdu (CN); Tianming Wang, Chengdu (CN); Wei Liu, Chengdu (CN); Baolei Zhang, Chengdu (CN); Mingliang Zhao, Chengdu (CN); Yufeng Liang, Chengdu (CN); Jiaqiang Cai, Chengdu (CN); Lichun Wang, Chengdu (CN); Jingyi Wang, Chengdu (CN)

(73) Assignee: SICHUAN KELUN-BIOTECH BIOPHARMACEUTICAL CO., LTD., Sichuan (CN)

( * ) Notice: Subject to any disclaimer, the term of this patent is extended or adjusted under 35 U.S.C. 154(b) by 0 days.

(21) Appl. No.: 17/047,000

(22) PCT Filed: Jun. 3, 2019

(86) PCT No.: PCT/CN2019/089744
§ 371 (c)(1),
(2) Date: Oct. 12, 2020

(87) PCT Pub. No.: WO2019/237957
PCT Pub. Date: Dec. 19, 2019

(65) Prior Publication Data
US 2021/0179647 A1 Jun. 17, 2021

(30) Foreign Application Priority Data

Jun. 12, 2018 (CN) .......................... 201810600569.X

(51) Int. Cl.
C07F 9/6561 (2006.01)
C07F 9/02 (2006.01)

(52) U.S. Cl.
CPC .......... C07F 9/65616 (2013.01); C07F 9/025 (2013.01); C07B 2200/13 (2013.01)

(58) Field of Classification Search
None
See application file for complete search history.

(56) References Cited

U.S. PATENT DOCUMENTS 10,899,786 B2 * 1/2021 Cai ........................... A61P 1/16
2020/0308214 A1 * 10/2020 Cai ........................... A61P 35/00

FOREIGN PATENT DOCUMENTS

CN 105504007 A 4/2016
CN 106317116 A 1/2017

| WO | 2008005555 A1 | 1/2008 |
| WO | 2010075549 A2 | 7/2010 |
| WO | 2011130557 A2 | 10/2011 |
| WO | 2013025788 A1 | 2/2013 |
| WO | 2014076490 A1 | 5/2014 |

(Continued)

OTHER PUBLICATIONS

Chapman et al., Purification of PMPA Amidate Prodrugs by SMB Chromatography and X-Ray Crystallography of the Diastereomerically Pure GS-7340, Nucleosides, Nucleotides & Nucleic Acids, vol. 20, No. 4-7, Apr.-Jul. 2001, pp. 1085-1090.

(Continued)

Primary Examiner — Joseph R Kosack
(74) Attorney, Agent, or Firm — Kilpatrick Townsend & Stockton LLP

(57) ABSTRACT

The present invention relates to compounds represented by formula (I) and formula (II) and a chiral synthesis and chiral isolation method therefor, further relating to a salt and crystal form of the compound represented by formula (I), a preparation method therefor, a pharmaceutical composition comprising the same, and use thereof in the preparation of a medicament used for the treatment of a viral infectious disease such as hepatitis B.

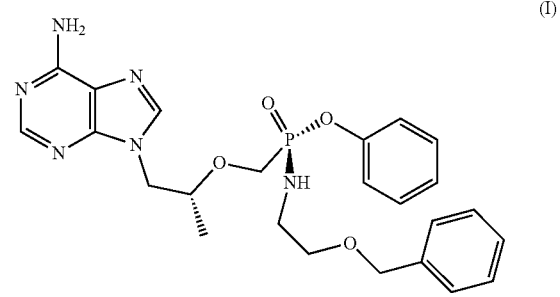

(I)

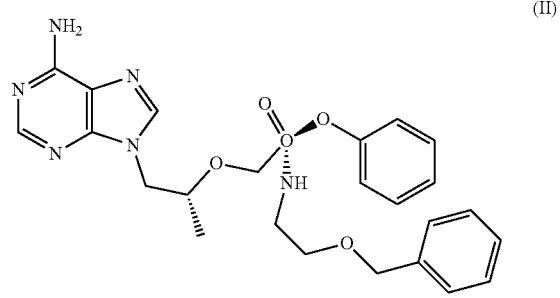

(II)

25 Claims, 16 Drawing Sheets

(56) References Cited

FOREIGN PATENT DOCUMENTS

| WO | 2014143643 A1 | 9/2014 |
| WO | 2015127848 A1 | 9/2015 |
| WO | 2016044281 A1 | 3/2016 |
| WO | 2018113652 A1 | 6/2018 |

OTHER PUBLICATIONS

Krecmerova et al., New Prodrugs of Two Pyrimidine Acyclic Nucleoside Phosphonates: Synthesis and Antiviral Activity, Bioorganic & Medicinal Chemistry, vol. 25, No. 17, Jul. 6, 2017, pp. 4637-4648.
International Application No. PCT/CN2019/089744, International Search Report, and Written Opinion dated Sep. 6, 2019, 12 pages.

* cited by examiner

PHOSPHONAMIDE ESTER COMPOUND, SALT THEREOF, RELATED CRYSTAL FORM THEREOF, PREPARATION METHOD THEREFOR AND USE THEREOF

CROSS REFERENCE TO RELATED APPLICATIONS

This application is a 371 National Phase Application of PCT/CN2019/089744, filed Jun. 3, 2019, which application claims the benefit of priority of Chinese Patent Application No. 201810600569.X filed on Jun. 12, 2018, the disclosures of which are incorporated herein by reference in their entireties.

FIELD OF THE INVENTION

The present invention relates to (S)—P—((((R)-1-(6-amino-9H-purin-9-yl)propan-2-yl)oxy)methyl)-phenoxy-N-(2-(benzyloxy)ethyl)-phosphonamide (hereinafter referred to as "the compound of Formula (I)") and (R)—P—((((R)-1-(6-amino-9H-purin-9-yl) propan-2-yl)oxy)methyl)-phenoxy-N-(2-(benzyloxy)ethyl)-phosphonamide (hereinafter referred to as "the compound of Formula (II)") and methods for chiral synthesis and chiral isolation of the same, and also to salts of the "compound of Formula (I)" and crystalline forms thereof and methods for preparing the same, a pharmaceutical composition comprising the same, and use thereof in the manufacture of a medicament for preventing or treating viral infectious diseases such as hepatitis B.

BACKGROUND OF THE INVENTION

Hepatitis B virus is a DNA virus belonging to the hepadnaviridae family, and its DNA synthesis depends on hepatitis B virus DNA polymerase. Use of DNA polymerase inhibitors as anti-hepatitis B virus drugs has become a very competitive option. Tenofovir (PMPA), an inhibitor of nucleotide DNA polymerase and reverse transcriptase, has anti-HBV and HIV activity, and its phosphonate derivative Tenofovir disoproxil fumarate (TDF) and phosphonamide ester derivative Tenofovir alafenamide (TAF) have been approved by FDA for treating human immunodeficiency syndrome and hepatitis B virus. TAF overcomes the disadvantage of poor plasma stability of TDF. TAF mainly produces an adenosine triphosphate analogue in hepatocytes through esterase hydrolysis, phosphorylation and other actions, and the adenosine triphosphate analogue is inserted into newly generated DNA chains, thereby blocking DNA polymerase-catalyzed DNA synthesis and inhibiting virus replication (WO2013025788 A1; Nucleosides Nucleotides Nucleic Acids, 2001, 20, 1085-1090). However, in the phase III clinical trial, although TAF had a significant improvement in terms of alanine aminotransferase (ALT) recovery, bone metabolism and renal function compared with TDF, there were still problems such as the following: the ALT recovery rate was lower than 80%; the spinal bone mineral density (BMD) decreased by more than 5% in more than 10% of patients; and the glomerular filtration rate decreased by more than 25% in more than 10% of patients. These problems are unmet clinical needs, so there is an urgent need for a new generation of therapeutic drugs which are more effective and safer.

The International Patent Application No. PCT/CN2017/117126 filed by the applicant discloses a series of phosphonamide ester compounds having novel structures, which, as Tenofovir prodrugs, can be rapidly metabolized into Tenofovir, and have good in vivo and in vitro pharmacokinetic and pharmacodynamic properties.

SUMMARY OF THE INVENTION

An aspect of the present invention provides compounds of Formula (I) and Formula (II) as shown below:

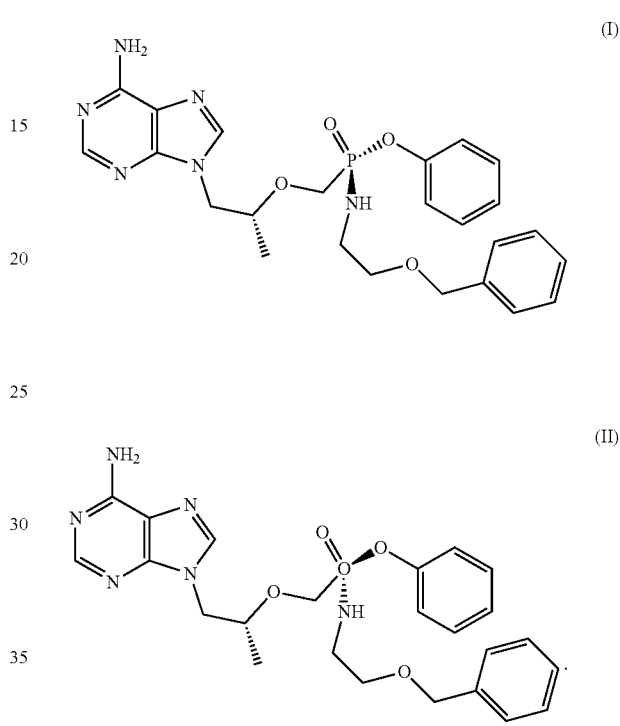

Another aspect of the present invention provides a method for the synthesis and chiral isolation of the racemates of the compounds of Formula (I) and Formula (II) as shown in the following reaction scheme:

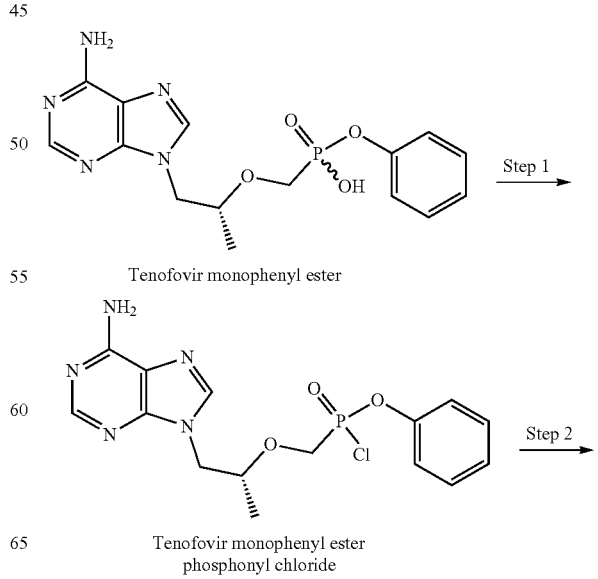

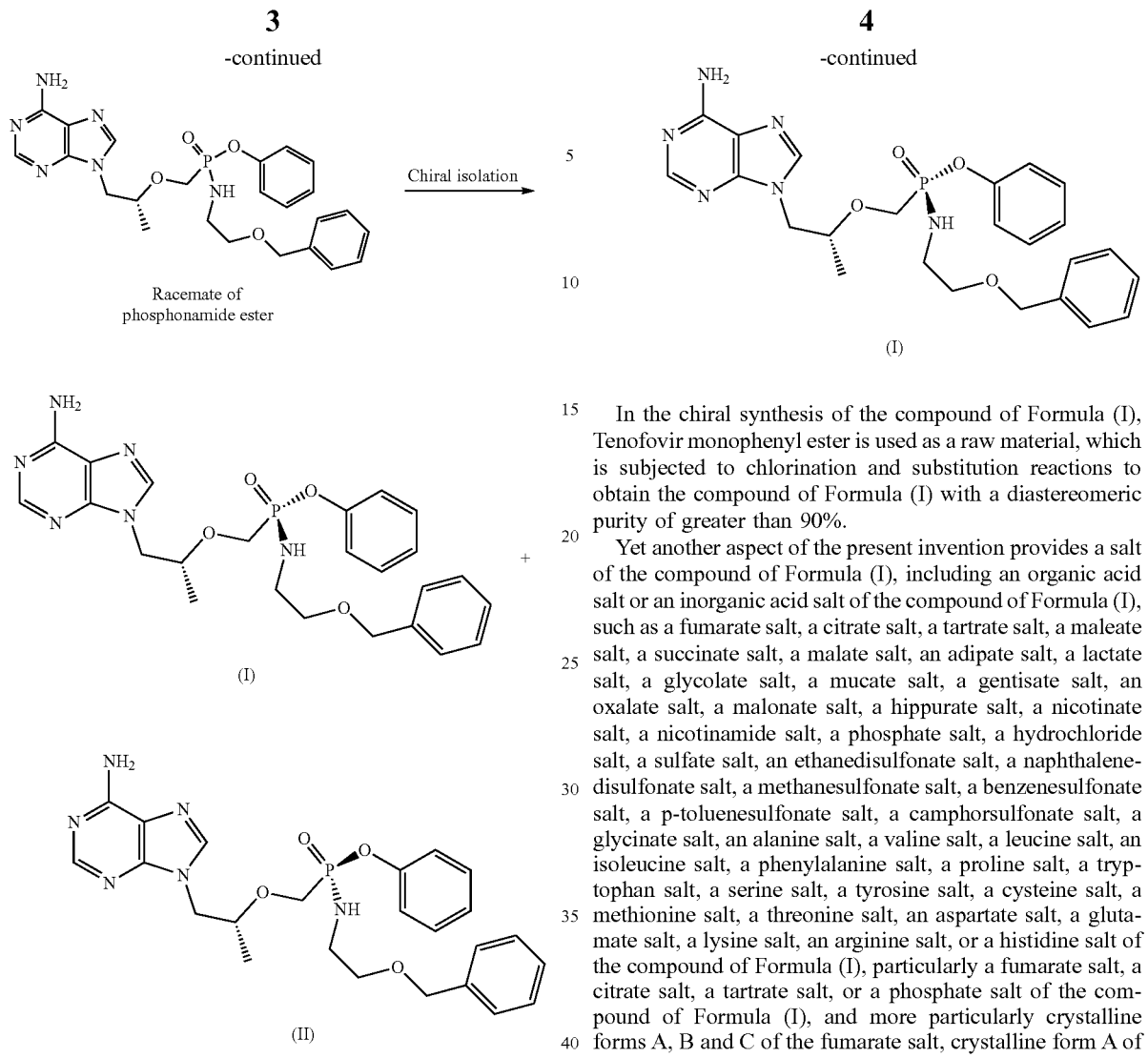

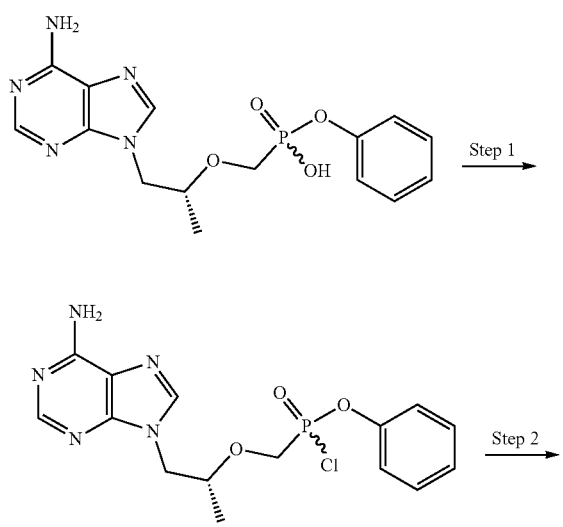

In the chiral synthesis of the compound of Formula (I), Tenofovir monophenyl ester is used as a raw material, which is subjected to chlorination and substitution reactions to obtain the compound of Formula (I) with a diastereomeric purity of greater than 90%.

Yet another aspect of the present invention provides a salt of the compound of Formula (I), including an organic acid salt or an inorganic acid salt of the compound of Formula (I), such as a fumarate salt, a citrate salt, a tartrate salt, a maleate salt, a succinate salt, a malate salt, an adipate salt, a lactate salt, a glycolate salt, a mucate salt, a gentisate salt, an oxalate salt, a malonate salt, a hippurate salt, a nicotinate salt, a nicotinamide salt, a phosphate salt, a hydrochloride salt, a sulfate salt, an ethanedisulfonate salt, a naphthalene-disulfonate salt, a methanesulfonate salt, a benzenesulfonate salt, a p-toluenesulfonate salt, a camphorsulfonate salt, a glycinate salt, an alanine salt, a valine salt, a leucine salt, an isoleucine salt, a phenylalanine salt, a proline salt, a tryptophan salt, a serine salt, a tyrosine salt, a cysteine salt, a methionine salt, a threonine salt, an aspartate salt, a glutamate salt, a lysine salt, an arginine salt, or a histidine salt of the compound of Formula (I), particularly a fumarate salt, a citrate salt, a tartrate salt, or a phosphate salt of the compound of Formula (I), and more particularly crystalline forms A, B and C of the fumarate salt, crystalline form A of the citrate salt, crystalline forms A and B of the tartrate salt, and crystalline forms A and B of the phosphate salt of the compound of Formula (I). Preferably, in the salt of the compound of Formula (I), the molar ratio of the compound of Formula (I) to the inorganic acid or the organic acid is 1:1 or 1:½ or 1:⅓, particularly preferably 1:1.

The compound of Formula (I) and salts thereof provided by the present invention have the following advantages: as prodrugs, they can be rapidly metabolized into the active substance in animals, thereby inhibiting the reverse transcriptase and DNA polymerase of the HBV virus, so that the effect of inhibiting HBV DNA replication is achieved. The salts of the compound of Formula (I) provided by the invention have good manufacturability (easy to prepare), with low solvent residue in the crystalline forms of various salts. The acids used in the formation of the salts of the present invention have high safety without causing undesirable toxicity. The salts of the compound of Formula (I) provided by the invention have good safety in animal tests with no obvious influence on liver, kidney, bone metabolism and the like, and thus are expected to reduce the side effects caused by long-term medication of patients, including abnormal liver function, reduced glomerular filtration rate, pain and osteoporosis caused by reduced bone density and the like. In addition, the various salts and crystalline forms thereof according to the present invention are easier to prepare in large scale in high purity, thus more suitable for use in the preparation of pharmaceutical formulations, and can also exhibit other advantageous physical properties (e.g., good solubility, low hygroscopicity (moisture absorption), good solid state stability, etc.) as well as pharmacokinetic properties (e.g., different crystal lattices increase dissolution rate and bioavailability), etc.

Yet another aspect of the present invention provides a method for preparing the salt of the compound of Formula (I), comprising reacting the compound of Formula (I) in any solid form with an inorganic acid or an organic acid, precipitating solid, and subsequently separating and drying the precipitated solid. The methods for precipitating solid include, but are not limited to, a gas-solid permeation method, an anti-solvent crystallization method, a room temperature suspension stirring method, a high temperature suspension stirring method, a gas-liquid permeation method, a room temperature slow volatilization method, a slow cooling method, and the like.

Yet another aspect of the present invention provides a pharmaceutical composition comprising a salt of the compound of Formula (I) as described above (e.g., a fumarate salt, a citrate salt, a tartrate salt or a phosphate salt of the compound of Formula (I), particularly the crystals of the fumarate salt, citrate salt, tartrate salt or phosphate salt of the compound of Formula (I), and more particularly the crystals of the fumarate salt of the compound of Formula (I)) or any combination thereof, and one or more pharmaceutically acceptable carriers.

Yet another aspect of the present invention provides a method for treating viral infectious diseases such as hepatitis B in a subject, comprising administering to a subject in need thereof a therapeutically effective amount of the compound of Formula (I) or a salt thereof as described above (e.g., a fumarate salt, a citrate salt, a tartrate salt or a phosphate salt of the compound of Formula (I), particularly the crystals of the fumarate salt, citrate salt, tartrate salt or phosphate salt of the compound of Formula (I), and more particularly the crystals of the fumarate salt of the compound of Formula (I)) or any combination thereof.

Yet another aspect of the present invention provides the compound of Formula (I) or a salt thereof as described above (e.g., a fumarate salt, a citrate salt, a tartrate salt or a phosphate salt of the compound of Formula (I), particularly the crystals of the fumarate salt, citrate salt, tartrate salt or phosphate salt of the compound of Formula (I), and more particularly the crystals of the fumarate salt of the compound of Formula (I)) or any combination thereof for use in treating viral infectious diseases such as hepatitis B in a subject.

Yet another aspect of the present invention provides use of the compound of Formula (I) or a salt thereof as described above (e.g., a fumarate salt, a citrate salt, a tartrate salt or a phosphate salt of the compound of Formula (I), particularly the crystals of the fumarate salt, citrate salt, tartrate salt or phosphate salt of the compound of Formula (I), and more particularly the crystals of the fumarate salt of the compound of Formula (I)) or any combination thereof in the manufacture of a medicament for treating viral infectious diseases such as hepatitis B in a subject.

The crystals of the salts of the compounds of Formula (I) according to the invention have one or more of the following advantageous properties:

i) They have high solubility, high dissolution rate, low hygroscopicity, high flowability or significantly improved viscosity.

ii) They have excellent physicochemical stabilities including, but not limited to, light stability, thermal stability, high humidity resistance, and the like. For example, good light stability can ensure the reliability of the crystals during storage and transportation, thereby ensuring the safety of the formulation, so that it is not needed to specially package the crystals for preventing the influence of light, thereby reducing the costs; the crystals will not be degraded by the influence of light, thereby improving the safety of the formulation and the effectiveness after long-term storage; and the patient taking the crystals will not worry about the photosensitive reaction of the formulation caused by exposure to sunlight. Good thermal stability allows the crystals to remain stable for a long time, and to be suitable for use in standard formulation production processes. Good physicochemical stability makes the crystals easier to prepare and more suitable for the production of formulations.

iii) They have improved metabolism, improved bioavailability, reduced toxicity or improved safety.

iv) They are suitable and convenient for mass production, and have reduced cost.

DETAILED DESCRIPTION OF THE INVENTION

Definitions

Figure 1:
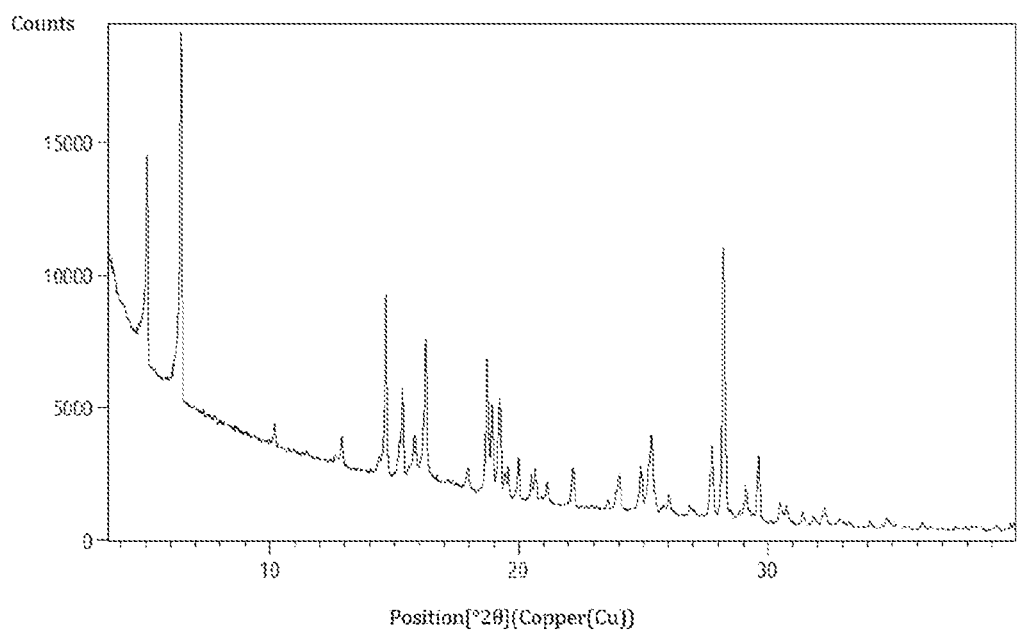
FIG. 1 shows an XRPD pattern of crystalline form A of the fumarate salt of the compound of Formula (I).

Unless otherwise defined in the context, all technical and scientific terms used herein are intended to have the same meaning as commonly understood by a person skilled in the art. References to techniques employed herein are intended to refer to the techniques as commonly understood in the art, including variations on those techniques or substitutions of equivalent techniques which would be apparent to a person skilled in the art. While it is believed that most of the following terms will be readily understood by a person skilled in the art, the following definitions are nevertheless put forth to better illustrate the present invention.

The terms "contain", "include", "comprise", "have", or "relate to", as well as other variations used herein are inclusive or open-ended, and do not exclude additional, unrecited elements or method steps.

The word "about" as used herein refers to, as appreciated by a person skilled in the art, a range within the acceptable standard error of a value, such as ±0.05, ±0.1, ±0.2, ±0.3, ±1, ±2 or ±3, etc.

As used herein, the term "salt of the compound of Formula (I)" includes an inorganic acid salt or an organic acid salt of the compound of Formula (I), such as, but not limited to, a fumarate salt, a citrate salt, a tartrate salt, a maleate salt, a succinate salt, a malate salt, an adipate salt, a lactate salt, a glycolate salt, a mucate salt, a gentisate salt, an oxalate salt, a malonate salt, a hippurate salt, a nicotinate salt, a nicotinamide salt, a phosphate salt, a hydrochloride salt, a sulfate salt, an ethanedisulfonate salt, a naphthalenedisulfonate salt, a methanesulfonate salt, a benzenesulfonate salt, a p-toluenesulfonate salt, a camphorsulfonate salt, a glycinate salt, an alanine salt, a valine salt, a leucine salt, an isoleucine salt, a phenylalanine salt, a proline salt, a tryptophan salt, a serine salt, a tyrosine salt, a cysteine salt, a methionine salt, a threonine salt, an aspartate salt, a glutamate salt, a lysine salt, an arginine salt, and a histidine salt of the compound of Formula (I).

The term "solid form" as used herein includes all solid forms of the compound of Formula (I) and the salt thereof, such as a crystalline form or amorphous form.

The term "amorphous" as used herein refers to any solid substance which lacks order in three dimensions. In some instances, amorphous solids may be characterized by known techniques, including XRPD crystallography, solid state nuclear magnet resonance (ssNMR) spectroscopy, DSC, or some combination of these techniques. As illustrated below, amorphous solids give diffuse XRPD patterns, typically comprised of one or two broad peaks (i.e., peaks having base widths of about 5° 2θ or greater).

The term "crystalline form" or "crystal" as used herein refers to any solid substance exhibiting three-dimensional order, which in contrast to an amorphous solid substance, gives a distinctive XRPD pattern with sharply defined peaks.

The term "X-ray powder diffraction pattern (XRPD pattern)" as used herein refers to the experimentally observed diffractogram or parameters derived therefrom. XRPD patterns are usually characterized by peak positions (abscissa) and peak intensities (ordinate).

The term "2θ" as used herein refers to the peak position in degrees based on the experimental setup of the X-ray diffraction experiment and is a common abscissa unit in diffraction patterns. The experimental setup requires that if a reflection is diffracted when the incoming beam forms an angle theta (θ) with a certain lattice plane, the reflected beam is recorded at an angle 2 theta (2θ). It should be understood that reference herein to specific 2θ values for a specific solid form is intended to mean the 2θ values (in degrees) as measured using the X-ray diffraction experimental conditions as described herein.

The term "thermogravimetric analysis (TGA) graph" as used herein refers to a curve recorded on a thermogravimetric analyzer.

The term "differential scanning calorimetry (DSC) graph" as used herein refers to a curve recorded on a differential scanning calorimeter.

The term "nuclear magnetic resonance ($^1$H-NMR) spectrum" as used herein refers to signal peaks recorded on a nuclear magnetic resonance spectrometer.

As used herein, the term "essentially the same" with reference to X-ray diffraction peak positions means that typical peak position and intensity variability are taken into account. For example, one skilled in the art will appreciate that the peak positions (2θ) will show some variability, typically as much as 0.1 to 0.2 degree, as well as on the apparatus being used to measure the diffraction. Further, one skilled in the art will appreciate that relative peak intensities will show inter-apparatus variability as well as variability due to degree of crystallinity, preferred orientation, prepared sample surface, and other factors known to those skilled in the art, and should be taken as qualitative measures only. Similarly, as used herein, "essentially the same" with reference to the DSC graph and TGA graph is intended to also encompass the variabilities associated with these analytical techniques, which are known to those of skill in the art. For example, a differential scanning calorimetry graph will typically have a variability of up to ±0.2° C. for well defined peaks, and even larger for broad lines (e.g., up to ±1° C.).

The term "good solvent" as used herein means a solvent for dissolving the compound of Formula (I) or the salt thereof according to the present invention.

The term "anti-solvent" as used herein means a solvent for reducing the solubility of a substance to be crystallized in a good solvent.

The term "anti-solvent crystallization" as used herein means a method where a good solvent is used in combination with an anti-solvent, thereby reducing the solubility of a substance to be crystallized in the good solvent. According to the order of solvent addition, the anti-solvent crystallization can be classified into anti-solvent addition and reverse anti-solvent addition. The anti-solvent addition is a method where a substance to be crystallized is dissolved in a good solvent and then an anti-solvent is added thereto to crystallize, and the reverse anti-solvent addition is a method where a substance to be crystallized is dissolved in a good solvent and then the resulting solution is added to an anti-solvent to crystallize.

The term "hydrocarbons" as used herein preferably means hydrocarbons having 1 to 10 carbon atoms, including alkanes, halogenated alkanes, alkenes, alkynes, and aromatic hydrocarbons, specifically including, but not limited to, dichloromethane, trichloromethane (chloroform), n-hexane, n-heptane and toluene.

The term "alcohols" as used herein preferably means alcohols having 1 to 10 carbon atoms, including, but not limited to, methanol, ethanol, 1-propanol (n-propanol), 2-propanol (isopropanol), 1-butanol, 2-butanol and tert-butanol.

The term "ethers" as used herein preferably means ethers having 2 to 6 carbon atoms, including chain ethers and cyclic ethers (e.g., furans (including tetrahydrofurans) and dioxanes), specifically including, but not limited to, diethyl ether, diisopropyl ether, methyl tert-butyl ether, tetrahydrofuran, 2-methyltetrahydrofuran, dioxane, cyclopentyl methyl ether, anisole and dimethoxy ethane.

The term "nitriles" as used herein preferably means nitriles having 2 to 6 carbon atoms, including, but not limited to, acetonitrile and propionitrile.

The term "ketones" as used herein preferably means ketones having 2 to 6 carbon atoms, including, but not limited to, acetone, butanone, methyl ethyl ketone, methyl isobutyl ketone, and diethyl ketone.

The term "esters" as used herein preferably means esters having 3 to 10 carbon atoms, including, but not limited to, ethyl acetate, propyl acetate, isopropyl acetate, ethyl isopropionate, dimethyl carbonate and butyl acetate.

The term "organic acids" as used herein preferably means organic acids having 1 to 10 carbon atoms, including, but not limited to, formic acid and acetic acid.

The term "sulfones" as used herein preferably means sulfones or sulfoxides having 2 to 10 carbon atoms, including, but not limited to, dimethyl sulfoxide.

The term "amides" as used herein preferably means amides having 1 to 10 carbon atoms, including, but not limited to, dimethylformamide or dimethylacetamide.

The term "nitrogen-containing heterocycles" as used herein preferably means nitrogen-containing heterocycles having 3 to 10 carbon atoms and at least one nitrogen atom, including, but not limited to, N-methylpyrrolidone.

Numerical ranges (e.g., "1 to 10") and subranges thereof (e.g., "2 to 10", "2 to 6", "3 to 10"), etc. as used herein encompass any point within the numerical range (for example, 1, 2, 3, 4, 5, 6, 7, 8, 9, or 10).

The chemical bond in the compound of the invention can be depicted herein with a solid line [ ——— ], a wavy line [ ⁓ ], a solid wedge [ ◤ ] or a dashed wedge [ ⫶⫶⫶⫶ ]. It is intended that a bond to an asymmetric atom depicted with a solid line indicates that all possible stereoisomers at the atom (e.g., specific enantiomers, racemic mixtures and the like) are contemplated. It is intended that a bond to an asymmetric atom depicted with a wavy line indicates that the bond is either a solid wedge [ ◤ ] bond or a dashed wedge [ ⫶⫶⫶⫶ ] bond. It is intended that a bond to an asymmetric atom depicted with a solid or dashed wedge indicates the existence of the stereoisomer that is shown. When present in a racemic mixture, a solid or dashed wedge is used to define relative stereochemistry rather than absolute stereochemistry.

It will be appreciated that slightly different DSC graphs may be given with different types of equipment or with different test conditions. The DSC graph can be determined, for example, using a Mettler Toledo DSC1 differential scanning calorimeter. As used herein, the term "essentially the same" with reference to the DSC graph means that typical characteristic peak positions are taken into account. For example, one skilled in the art will appreciate that the characteristic peak positions will show some variability, typically as much as 5° C. For a solid sample having polymorphism, the heating rate of the DSC test has a great effect on the DSC graph. At a relatively high heating rate, the thermal hysteresis effect of the instrument is obvious, and time is not enough for a crystalline form having a high melting point to recrystallize, so the DSC graph often only shows the melting endothermic peak of a crystalline form having a low melting point. At a moderate heating rate, the DSC graph shows two peaks: a melting endothermic peak of a crystalline form having a low melting point and a melting endothermic peak of a crystalline form having a high melting point. Only at a relatively low heating rate, the thermal hysteresis effect of the instrument is weak, and three peaks will appear: a melting endothermic peak of a crystalline form having a low melting point—a recrystallization exothermic peak—a melting endothermic peak of a crystalline form having a high melting point. It will be appreciated by those skilled in the art that determination of the ranges of heating rates corresponding to different DSC graphs described above will vary depending on the weights, shapes, particle sizes and particle size distributions of test samples (Reference: Giron D. Thermal analysis and calorimetric methods in the characterisation of polymorphs and solvates [J]. Thermochimica Acta, 1995, 248:1-59).

The prepared compound of Formula (I), salt of the compound of Formula (I), or crystalline form thereof may be recovered by methods including decantation, centrifugation, evaporation, gravity filtration, suction filtration, or any other technique for the recovery of solids under pressure or under reduced pressure. The recovered solid may optionally be dried. "Drying" in the present invention is carried out under reduced pressure (preferably in vacuum) until the residual solvent content is lowered within the limits given in the International Conference on Harmonisation of Technical Requirements for Registration of Pharmaceuticals for Human Use ("ICH") guidelines. The residual solvent content depends on the type of the solvent, but does not exceed about 5000 ppm, or preferably about 4000 ppm, or more preferably about 3000 ppm. Drying may be carried out in a tray dryer, vacuum oven, air oven, cone vacuum dryer, rotary vacuum dryer, fluidized bed dryer, spin flash dryer, flash dryer, or the like. The drying may be carried out at temperatures less than about 100° C., less than about 80° C., less than about 60° C., less than about 50° C., less than about 30° C., or any other suitable temperatures, at atmospheric pressure or under a reduced pressure (preferably in vacuum) for any desired period (e.g., about 1, 2, 3, 5, 10, 15, 20, 24 hours or overnight) until the desired result is achieved, as long as the salt is not degraded in quality. The drying can be carried out any desired times until the desired product quality is achieved. The dried product may optionally be subjected to a size reduction procedure to produce desired particle sizes. Milling or micronization may be performed before drying, or after the completion of drying of the product. Techniques that may be used for particle size reduction include, without limitation, ball, roller and hammer milling, and jet milling.

The term "anhydrous crystalline form" as used herein preferably means a crystalline form wherein no water molecule is comprised as a structural element.

Compounds of Formula (I) and Formula (II) and Preparation Method Thereof

It is an object of the present invention to provide compounds of Formula (I) and Formula (II) as shown below and preparation methods thereof.

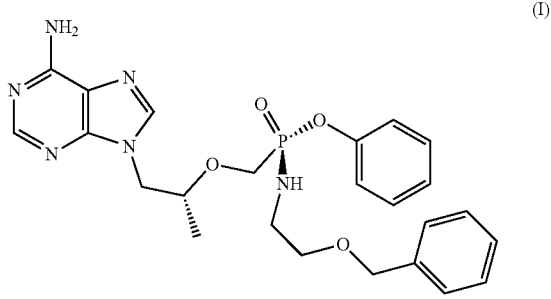 [SMILES: C[C@H](Cn1cnc2c(N)ncnc21)OC[P@@](=O)(NCCOCc1ccccc1)Oc1ccccc1]

(I)

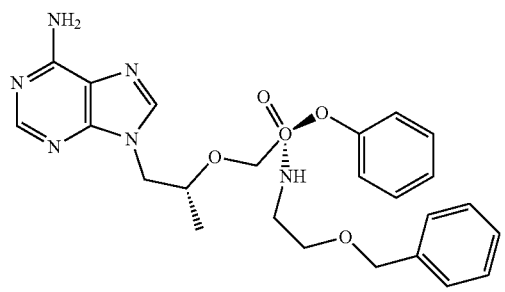

(II)

According to an embodiment, the present invention provides a method for synthesis and chiral isolation of racemates of the compounds of Formula (I) and Formula (II) as shown in the following scheme:

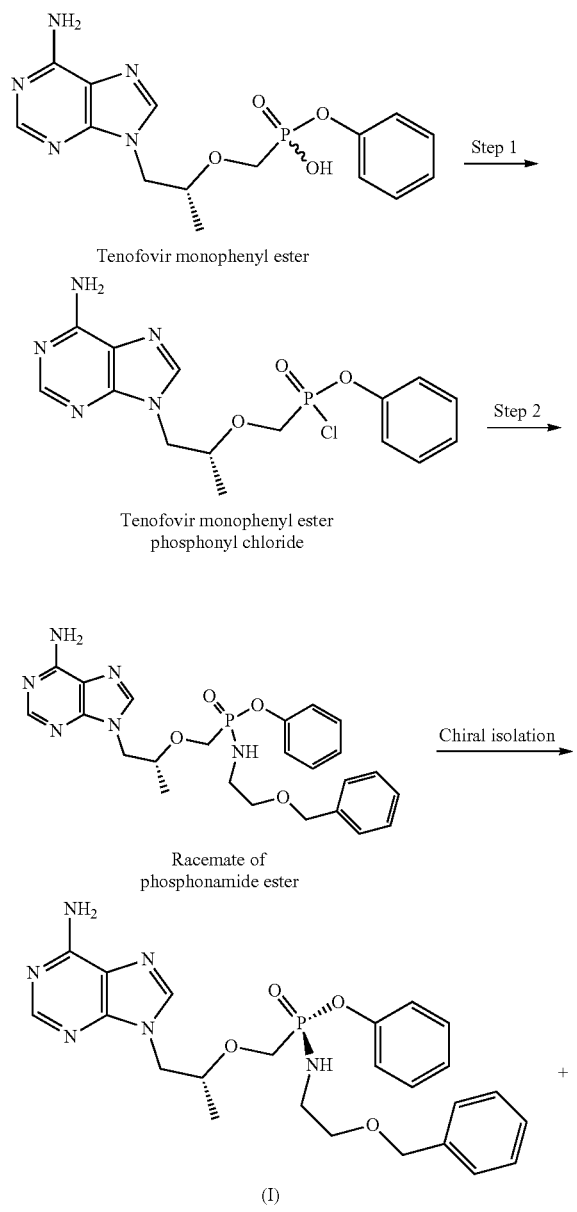

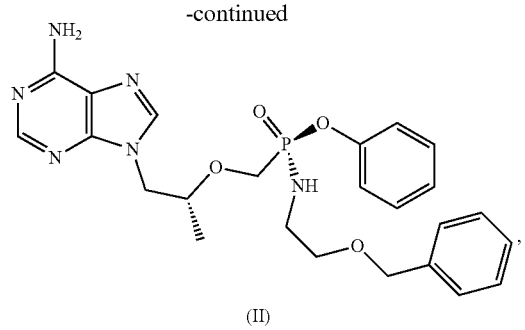

(II)

Step 1: reacting tenofovir monophenyl ester as a raw material with a chlorinating agent to obtain an intermediate tenofovir monophenyl ester phosphonyl chloride, wherein the chlorinating agent includes, but is not limited to, thionyl chloride, phosphorus oxychloride, phosphorus pentachloride, oxalyl chloride, and the like;

Step 2: reacting the tenofovir monophenyl ester phosphonyl chloride obtained in step 1 with 2-(benzyloxy)ethylamine to obtain a phosphonamide ester racemate; and Step 3: isolating the phosphonamide ester racemate obtained in step 2 by chiral chromatography to obtain the compounds of Formula (I) and Formula (II).

According to another embodiment, the present invention provides a chiral preparation method for the compound of Formula (I) as shown in the following reaction scheme:

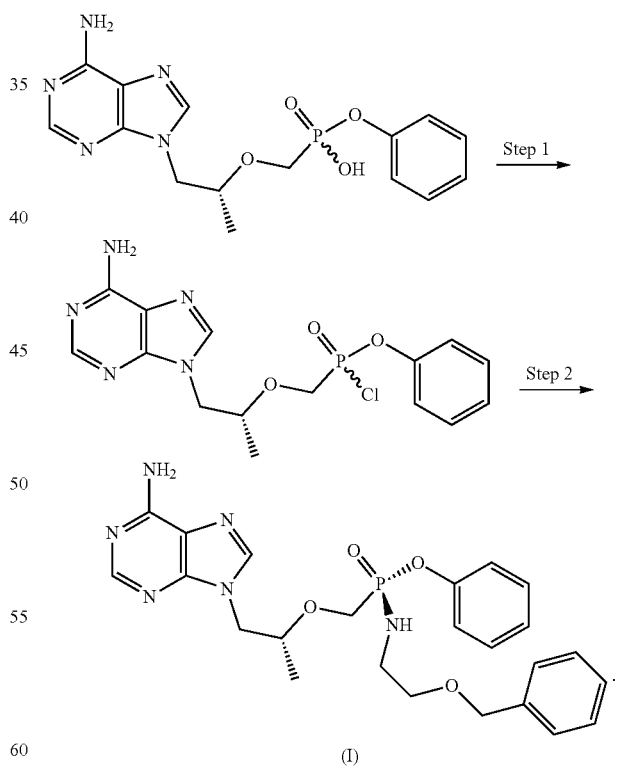

(I)

In a preferred embodiment of the chiral preparation method, step 1 comprises: reacting (((1R)-2-(6-amino-9H-purin-9-yl)-1-methylethoxy)methyl)phosphonic acid monophenyl ester (tenofovir monophenyl ester) with a chlorinating agent such as thionyl chloride, phosphorus oxychloride, phosphorus pentachloride and oxalyl chloride in a solvent such as toluene, xylene, anisole and acetonitrile at a temperature of 50-120° C. (preferably 80-110° C., more preferably 90-100° C.) to obtain an intermediate ((((R)-1-(6-amino-9H-purin-9-yl)-1-methyl-ethoxy)methyl) phenoxyphosphonyl chloride; and step 2 comprises: reacting the intermediate ((((R)-1-(6-amino-9H-purin-9-yl)-1-methyl-ethoxy)methyl)phenoxyphosphonyl chloride obtained in step 1 with 2-(benzyloxy)ethylamine to obtain the compound of Formula (I) having a diastereoisomeric purity of greater than 90%.

Salts of the Compound of Formula (Ia) and Crystalline Forms Thereof, and Preparation Method Thereof Fumarate Salt of the Compound of Formula (I)

It is an object of the present invention to provide a fumarate salt of the compound of Formula (I) as shown below:

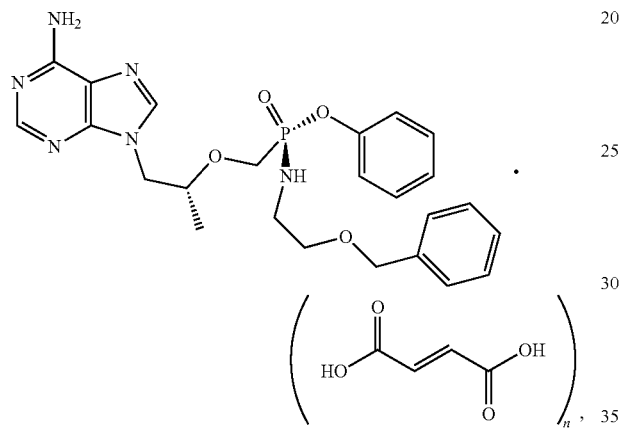

wherein n is 1 or ½, preferably 1. In other words, in the fumarate salt of the compound of Formula (I), the molar ratio of the compound of Formula (I) to fumaric acid is 1:1 or 1:½, preferably 1:1.

According to an embodiment, the present invention provides crystalline form A of the fumarate salt of the compound of Formula (I), wherein the molar ratio of the compound of Formula (I) to fumaric acid is 1:1. The crystalline form A of the fumarate salt of the compound of Formula (I) has an XRPD pattern comprising characteristic peaks at diffraction angles (2θ) of 5.1±0.2°, 6.4±0.2°, 16.3±0.2°, 18.7±0.2°, and 28.2±0.2°. In a preferred embodiment, the crystalline form A of the fumarate salt of the compound of Formula (I) has an XRPD pattern comprising characteristic peaks at diffraction angles (2θ) of 5.1±0.2°, 6.4±0.2°, 14.7±0.2°, 15.3±0.2°, 16.3±0.2°, 18.0±0.2°, 18.7±0.2°, 19.2±0.2°, 28.2±0.2°, and 29.6±0.2°. In a particularly preferred embodiment, the crystalline form A of the fumarate salt of the compound of Formula (I) has an XRPD pattern comprising peaks at the following diffraction angles (2θ):

| 2θ (°) ± 0.2° |
| --- |
| 5.1 |
| 6.4 |
| 12.9 |
| 14.7 |
| 15.3 |
| 16.3 |
| 18.0 |
| 18.7 |
| 18.9 |
| 19.2 |
| 20.0 |
| 20.7 |
| 22.2 |
| 24.0 |
| 24.9 |
| 25.3 |
| 27.8 |
| 28.2 |
| 29.6 |

In a particularly preferred embodiment, the crystalline form A of the fumarate salt of the compound of Formula (I) has an XRPD pattern comprising peaks at the following diffraction angles (2θ):

| 2θ (°) ± 0.2° | Intensity % |
| --- | --- |
| 5.1 | 59.1 |
| 6.4 | 100.0 |
| 12.9 | 17.8 |
| 14.7 | 45.0 |
| 15.3 | 32.4 |
| 16.3 | 39.9 |
| 18.0 | 25.6 |
| 18.7 | 31.8 |
| 18.9 | 19.4 |
| 19.2 | 29.1 |
| 20.0 | 11.4 |
| 20.7 | 11.2 |
| 22.2 | 11.3 |
| 24.0 | 13.5 |
| 24.9 | 12.7 |
| 25.3 | 17.6 |
| 27.8 | 18.8 |
| 28.2 | 73.8 |
| 29.6 | 21.2 |

In a particularly preferred embodiment, the crystalline form A of the fumarate salt of the compound of Formula (I) has an XRPD pattern comprising peaks at diffraction angles (2θ) essentially the same as shown in FIG. 1. In a particularly preferred embodiment, the crystalline form A of the fumarate salt of the compound of Formula (I) has XRPD peak positions essentially the same as shown in FIG. 1.

Figure 2:
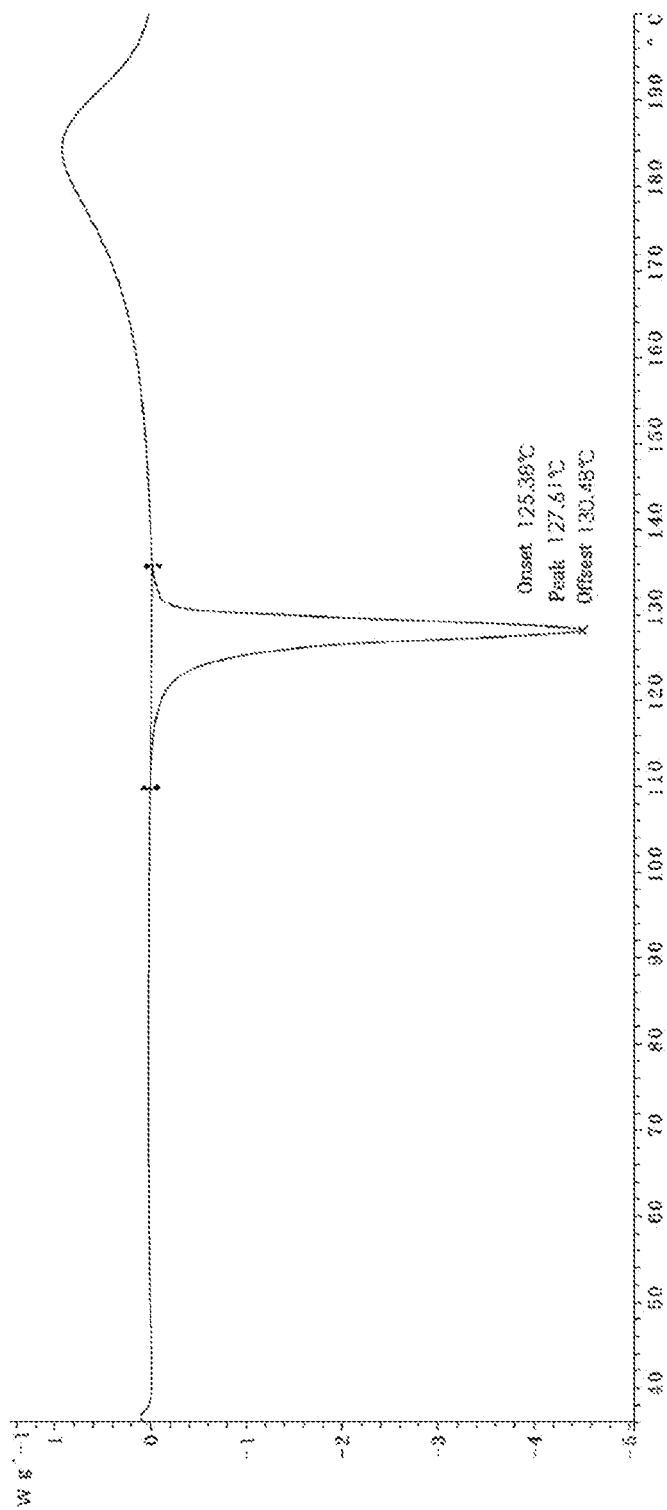
FIG. 2 shows a DSC graph of crystalline form A of the fumarate salt of the compound of Formula (I).
Figure 3:
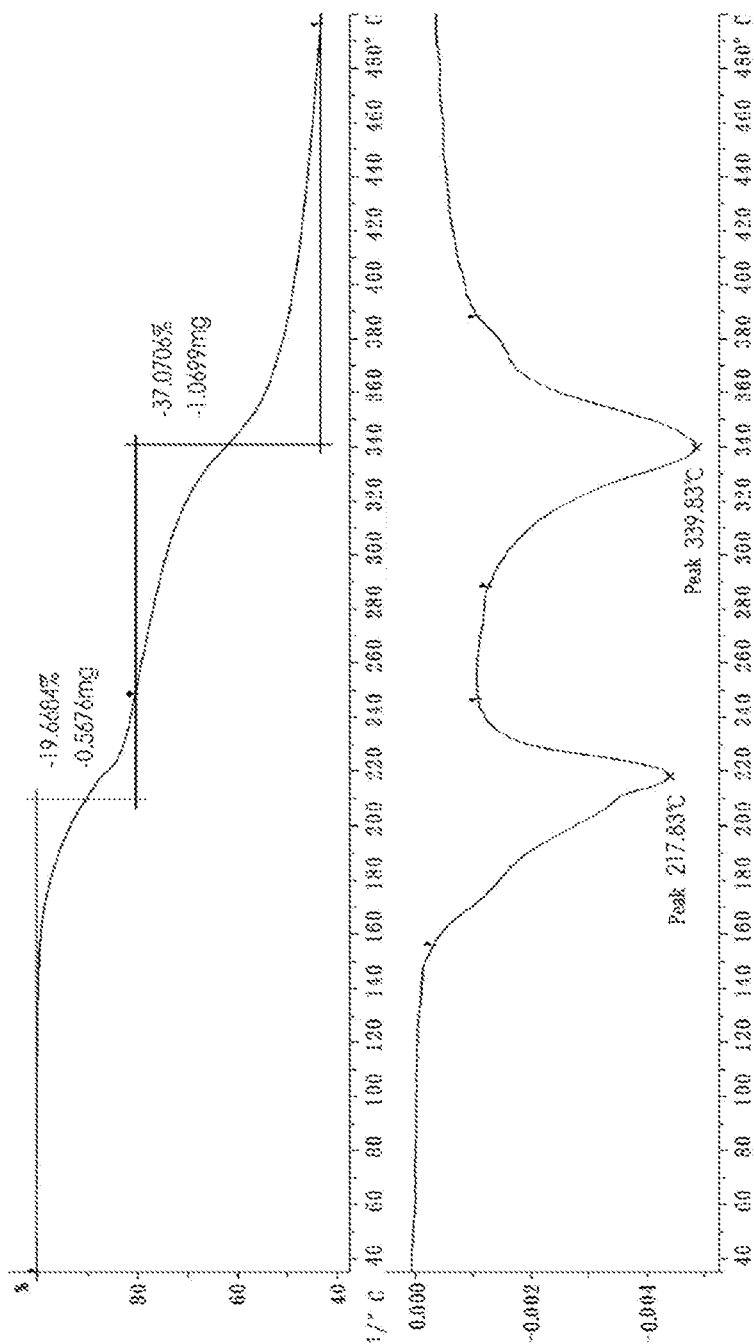
FIG. 3 shows a TGA graph of crystalline form A of the fumarate salt of the compound of Formula (I).

In a preferred embodiment, the crystalline form A of the fumarate salt of the compound of Formula (I) of the invention has a DSC graph comprising a characteristic peak at about 125±5° C. (the onset temperature), preferably about 125±2° C. (the onset temperature), and more preferably about 125±0.2° C. (the onset temperature). In a further preferred embodiment, the crystalline form A of the fumarate salt of the compound of Formula (I) of the invention has a DSC graph comprising a characteristic peak at a temperature essentially the same as shown in FIG. 2. In a particularly preferred embodiment, the characteristic peak position in the DSC graph of the crystalline form A of the fumarate salt of the compound of Formula (I) is essentially the same as shown in FIG. 2.

In a particularly preferred embodiment, the crystalline form A of the fumarate salt of the compound of Formula (I) of the present invention is in an unsolvated form. In a more preferred embodiment, the crystalline form A of the fumarate salt of the compound of Formula (I) of the invention is an anhydrous crystalline form.

In a preferred embodiment, the crystalline form A of the fumarate salt of the compound of Formula (I) of the present invention has the following cell parameters:

Cell Size:
a=13.6818(8) Å
b=6.3963(4) Å
c=17.2967(13) Å
α/°=90
β/°=96.113(6)
γ/°=90
Cell volume: 1505.06 (17) Å$^3$
Crystal system: monoclinic system
Space group: P2$_1$
Number of intramolecular asymmetric units: Z=2.

According to another embodiment, the present invention provides crystalline form B of the fumarate salt of the compound of Formula (I), wherein the molar ratio of the compound of Formula (I) to fumaric acid is 1:1. The crystalline form B of the fumarate salt of the compound of Formula (I) has an XRPD pattern comprising characteristic peaks at diffraction angles (2θ) of 10.2±0.2°, 10.8±0.2°, 17.1±0.2°, 18.8±0.2°, and 21.7±0.2°. In a preferred embodiment, the crystalline form B of the fumarate salt of the compound of Formula (I) has an XRPD pattern comprising characteristic peaks at diffraction angles (2θ) of 9.7±0.2°, 10.2±0.2°, 10.8±0.2°, 14.7±0.2°, 17.1±0.2°, 18.1±0.2°, 18.8±0.2°, 19.2±0.2°, 20.6±0.2°, and 21.7±0.2°. In a particularly preferred embodiment, the crystalline form B of the fumarate salt of the compound of Formula (I) has an XRPD pattern comprising peaks at the following diffraction angles (2θ):

| 2θ (°) ± 0.2° |
| --- |
| 9.7 |
| 10.2 |
| 10.8 |
| 11.8 |
| 13.2 |
| 13.8 |
| 14.7 |
| 16.1 |
| 17.1 |
| 18.1 |
| 18.8 |
| 19.2 |
| 20.6 |
| 21.7 |
| 22.3 |
| 23.8 |
| 26.7 |
| 27.0 |
| 27.5 |
| 29.3 |

In a particularly preferred embodiment, the crystalline form B of the fumarate salt of the compound of Formula (I) has an XRPD pattern comprising peaks at the following diffraction angles (2θ):

| 2θ (°) ± 0.2° | Intensity % |
| --- | --- |
| 9.7 | 33.0 |
| 10.2 | 100.0 |
| 10.8 | 72.1 |
| 11.8 | 10.2 |
| 13.2 | 12.6 |
| 13.8 | 17.9 |
| 14.7 | 18.7 |
| 16.1 | 18.5 |
| 17.1 | 47.9 |
| 18.1 | 33.4 |
| 18.8 | 53.2 |
| 19.2 | 28.7 |
| 20.6 | 36.0 |
| 21.7 | 39.1 |
| 22.3 | 16.6 |
| 23.8 | 10.2 |
| 26.7 | 18.1 |
| 27.0 | 14.4 |
| 27.5 | 10.8 |
| 29.3 | 12.1 |

Figure 4:
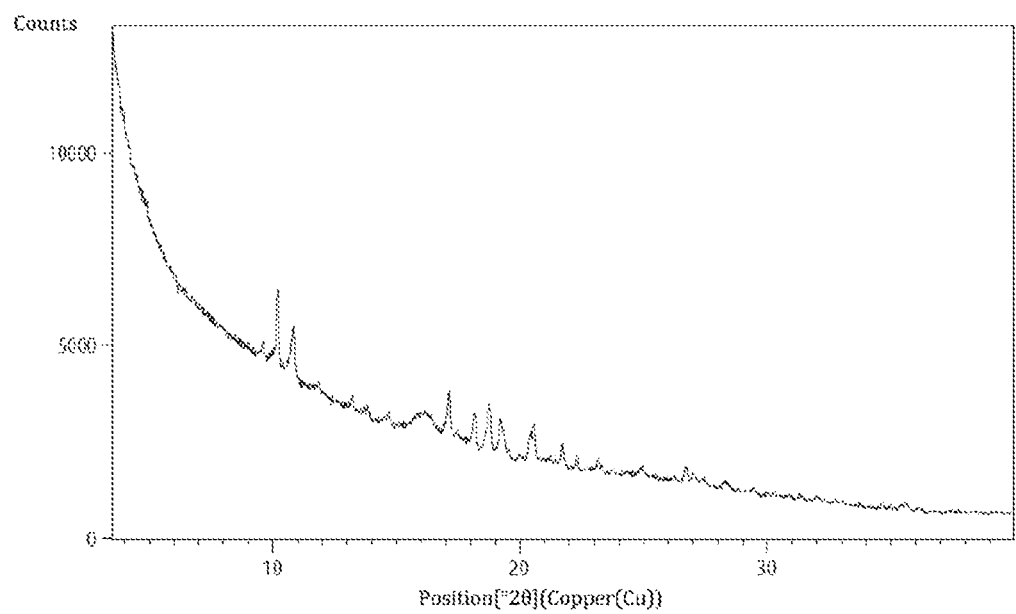
FIG. 4 shows an XRPD pattern of crystalline form B of the fumarate salt of the compound of Formula (I).

In a particularly preferred embodiment, the crystalline form B of the fumarate salt of the compound of Formula (I) has an XRPD pattern comprising peaks at diffraction angles (2θ) essentially the same as shown in FIG. 4. In a particularly preferred embodiment, the crystalline form B of the fumarate salt of the compound of Formula (I) has XRPD peak positions essentially the same as shown in FIG. 4.

According to another embodiment, the present invention provides crystalline form C of the fumarate salt of the compound of Formula (I), wherein the molar ratio of the compounds of Formula (I) to fumaric acid is 1:1. The crystalline form C of the fumarate salt of the compound of Formula (I) has an XRPD pattern comprising characteristic peaks at diffraction angles (2θ) of 4.3±0.2°, 6.8±0.2°, 14.3±0.2°, 18.8±0.2°, and 27.9±0.2°. In a preferred embodiment, the crystalline form C of the fumarate salt of the compound of Formula (I) has an XRPD pattern comprising characteristic peaks at diffraction angles (2θ) of 4.3±0.2°, 6.6±0.2°, 6.8±0.2°, 14.3±0.2°, 16.6±0.2°, 18.5±0.2°, 18.8±0.2°, 19.2±0.2°, 27.6±0.2°, and 27.9±0.2°. In a particularly preferred embodiment, the crystalline form C of the fumarate salt of the compound of Formula (I) has an XRPD pattern comprising peaks at the following diffraction angles (2θ):

| 2θ (°) ± 0.2° |
| --- |
| 4.3 |
| 6.6 |
| 6.8 |
| 13.0 |
| 14.3 |
| 15.3 |
| 15.8 |
| 16.2 |
| 16.6 |
| 17.3 |
| 18.5 |
| 18.8 |
| 19.2 |
| 20.1 |
| 22.6 |
| 23.3 |
| 25.8 |
| 26.2 |
| 27.6 |
| 27.9 |

In a particularly preferred embodiment, the crystalline form C of the fumarate salt of the compound of Formula (I) has an XRPD pattern comprising peaks at the following diffraction angles (2θ):

| 2θ (°) ± 0.2° | Intensity % |
| --- | --- |
| 4.3 | 100.0 |
| 6.6 | 20.4 |
| 6.8 | 32.1 |
| 13.0 | 11.2 |
| 14.3 | 31.0 |
| 15.3 | 12.2 |
| 15.8 | 15.4 |
| 16.2 | 20.2 |
| 16.6 | 26.4 |
| 17.3 | 10.4 |
| 18.5 | 22.5 |
| 18.8 | 47.5 |
| 19.2 | 27.3 |
| 20.1 | 11.8 |
| 22.6 | 13.8 |
| 23.3 | 11.0 |
| 25.8 | 15.4 |
| 26.2 | 11.8 |
| 27.6 | 27.5 |
| 27.9 | 33.6 |

Figure 5:
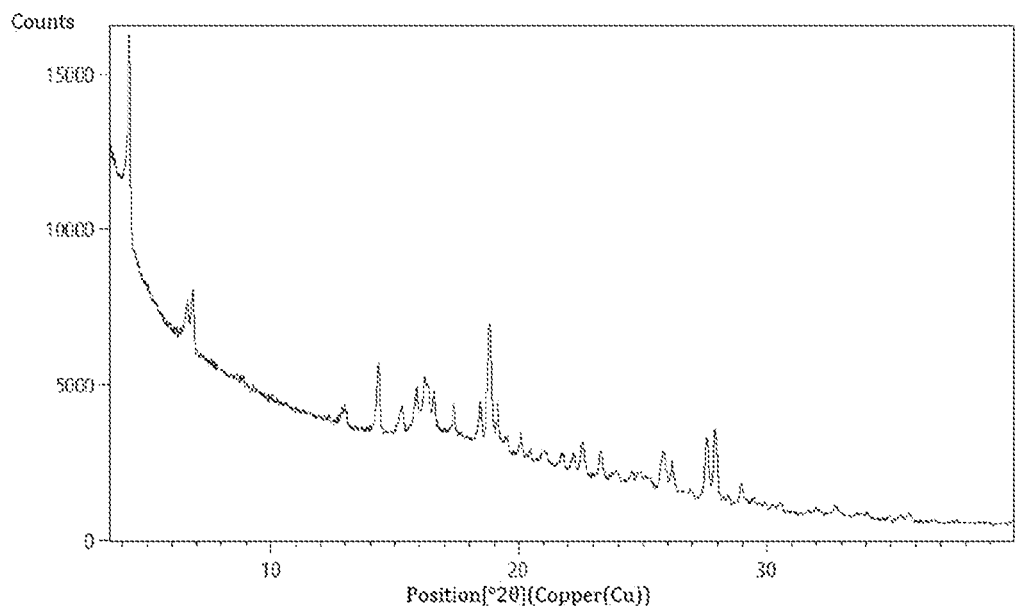
FIG. 5 shows an XRPD pattern of crystalline form C of the fumarate salt of the compound of Formula (I).

In a particularly preferred embodiment, the crystalline form C of the fumarate salt of the compound of Formula (I) has an XRPD pattern comprising peaks at diffraction angles (2θ) essentially the same as shown in FIG. 5. In a particularly preferred embodiment, the crystalline form C of the fumarate salt of the compound of Formula (I) has XRPD peak positions essentially the same as shown in FIG. 5.

Citrate Salt of the Compound of Formula (I)

It is an object of the present invention to provide a citrate salt of the compound of Formula (I) as shown below:

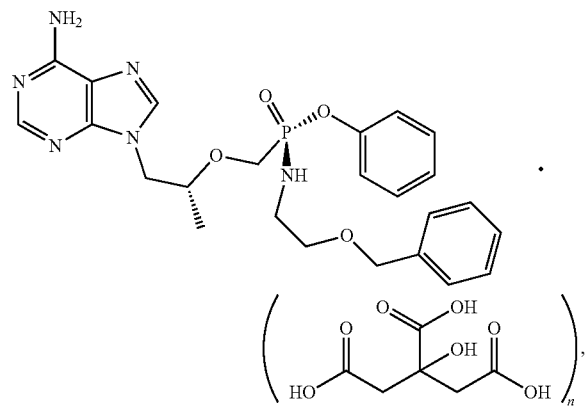

wherein n is 1 or ½ or ⅓, preferably 1. In other words, in the citrate salt of the compound of Formula (I), the molar ratio of the compound of Formula (I) to citric acid is 1:1 or 1:½ or 1:⅓, preferably 1:1.

According to an embodiment, the present invention provides crystalline form A of the citrate salt of the compound of Formula (I), wherein the molar ratio of the compound of Formula (I) to citric acid is 1:1. The crystalline form A of the citrate salt of the compound of Formula (I) has an XRPD pattern comprising characteristic peaks at diffraction angles (2θ) of 7.6±0.2°, 14.1±0.2°, 15.5±0.2°, 16.0±0.2°, and 20.7±0.2°. In a preferred embodiment, the crystalline form A of the citrate salt of the compound of Formula (I) has an XRPD pattern comprising characteristic peaks at diffraction angles (2θ) of 7.6±0.2°, 14.1±0.2°, 14.9±0.2°, 15.5±0.2°, 16.0±0.2°, 19.6±0.2°, 20.7±0.2°, 21.4±0.2°, 22.5±0.2°, and 24.5±0.2°. In a particularly preferred embodiment, the crystalline form A of the citrate salt of the compound of Formula (I) has an XRPD pattern comprising peaks at the following diffraction angles (2θ):

| 2θ (°) ± 0.2° | Intensity % |
| --- | --- |
| 7.6 | 35.7 |
| 14.1 | 38.6 |
| 14.9 | 23.8 |
| 15.5 | 57.3 |
| 16.0 | 100.0 |
| 19.6 | 13.3 |
| 20.7 | 63.5 |
| 21.4 | 20.5 |
| 22.5 | 26.3 |
| 24.5 | 22.9 |
| 28.5 | 6.3 |
| — | — |

Figure 6:
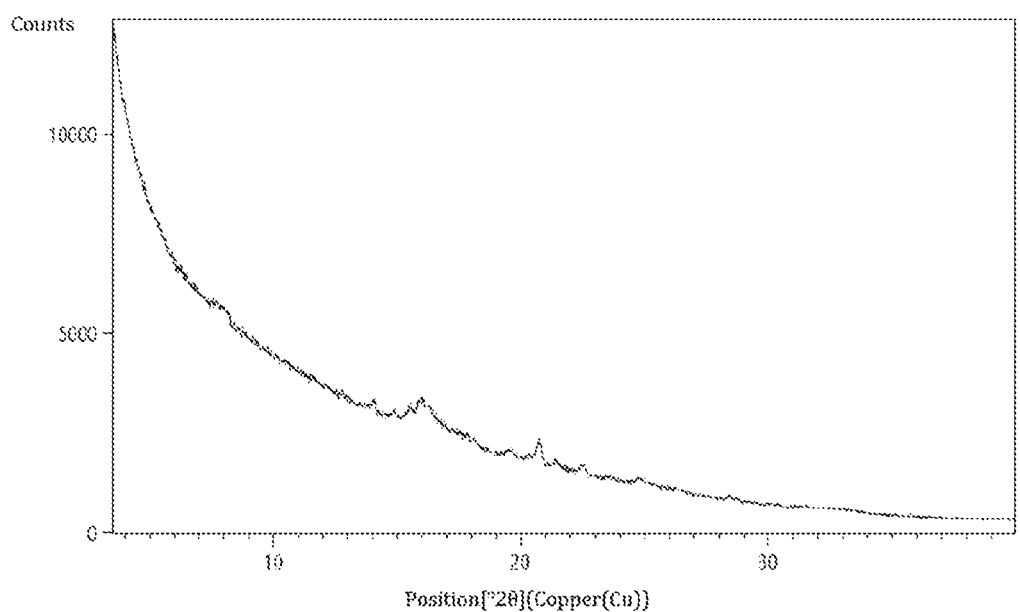
FIG. 6 shows an XRPD pattern of crystalline form A of the citrate salt of the compound of Formula (I).

In a particularly preferred embodiment, the crystalline form A of the citrate salt of the compound of Formula (I) has an XRPD pattern comprising peaks at diffraction angles (2θ) essentially the same as shown in FIG. 6. In a particularly preferred embodiment, the crystalline form A of the citrate salt of the compound of Formula (I) has XRPD peak positions essentially the same as shown in FIG. 6.

Figure 7:
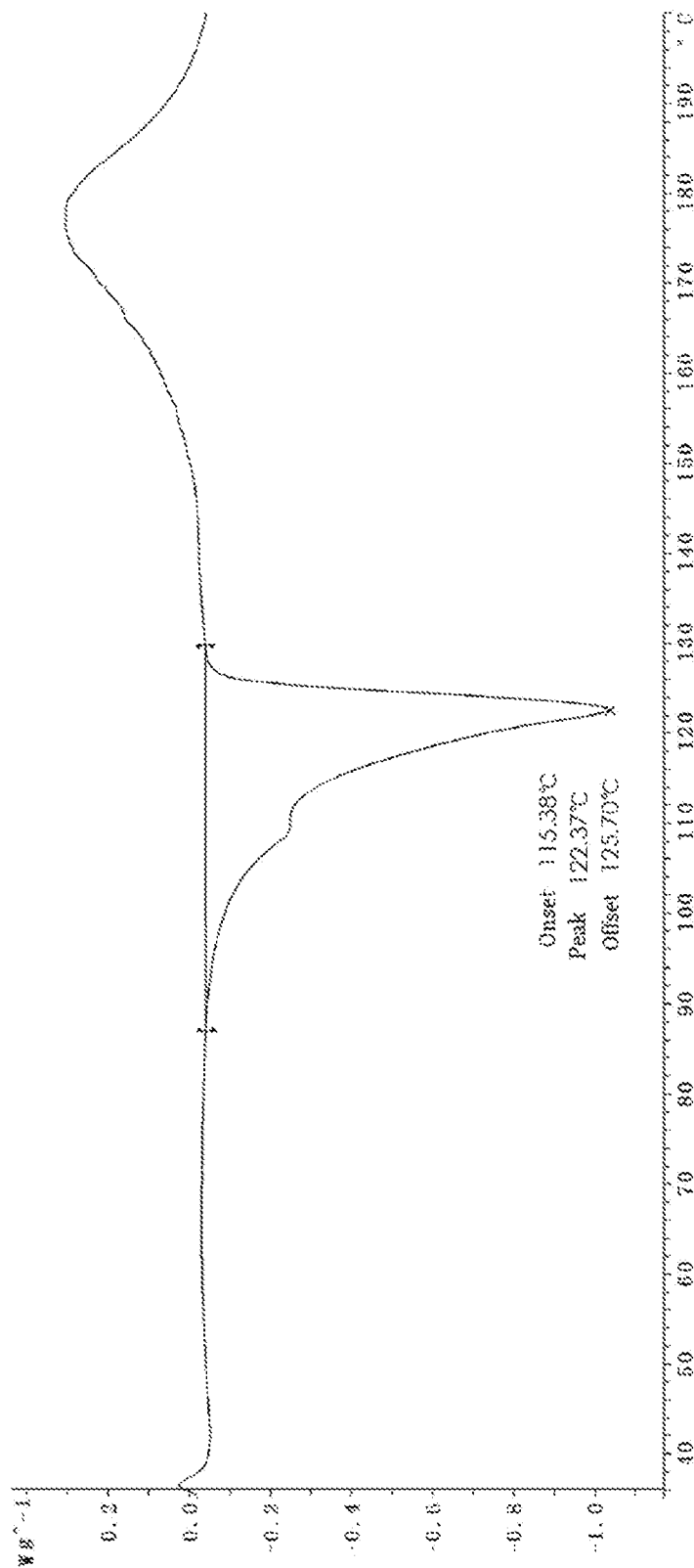
FIG. 7 shows a DSC graph of crystalline form A of the citrate salt of the compound of Formula (I).
Figure 8:
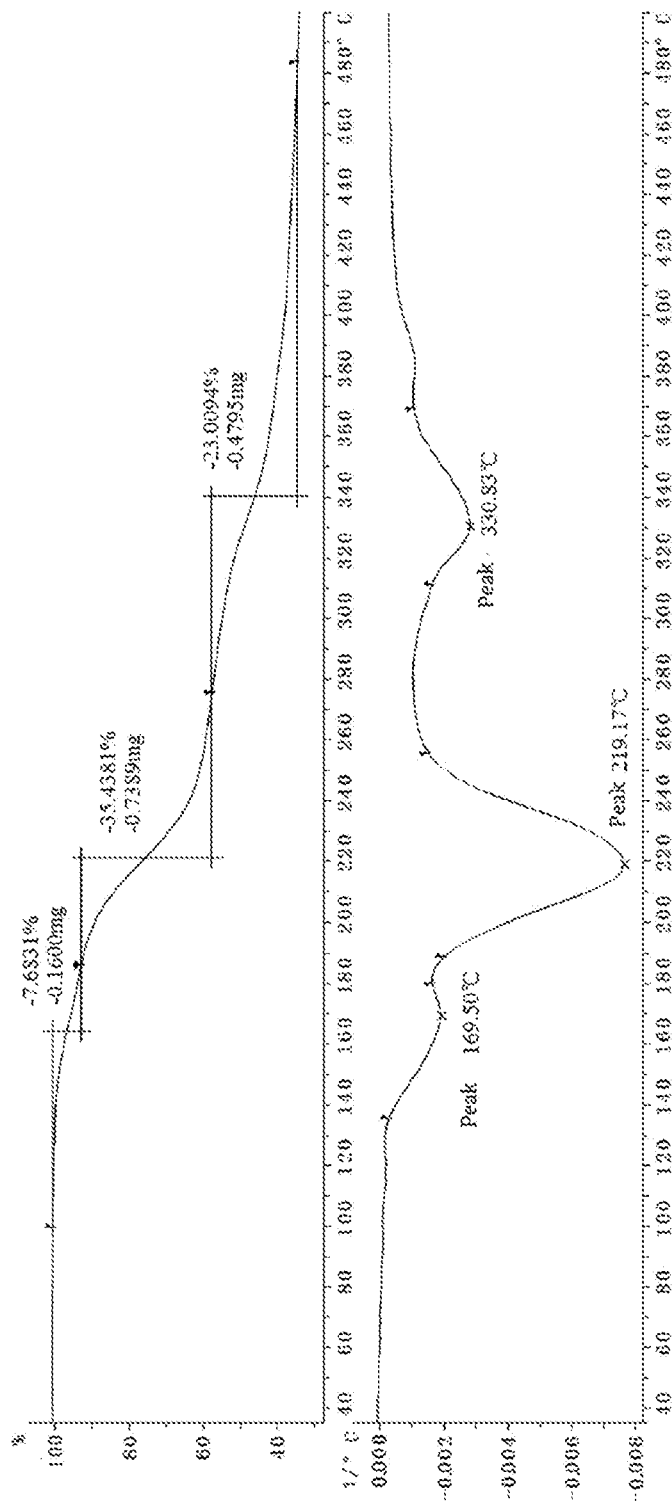
FIG. 8 shows a TGA graph of crystalline form A of the citrate salt of the compound of Formula (I).

In a preferred embodiment, the crystalline form A of the citrate salt of the compound of Formula (I) of the invention has a DSC graph comprising a characteristic peak at about 115±5° C. (the onset temperature), preferably about 115±2° C. (the onset temperature), and more preferably about 115±0.2° C. (the onset temperature). In a further preferred embodiment, the crystalline form A of the citrate salt of the compound of Formula (I) has a DSC graph comprising a characteristic peak at a temperature essentially the same as shown in FIG. 7. In a particularly preferred embodiment, the characteristic peak position in the DSC graph of the crystalline form A of the citrate salt of the compound of Formula (I) is essentially the same as shown in FIG. 7.

In a particularly preferred embodiment, the crystalline form A of the citrate salt of the compound of Formula (I) of the present invention is in an unsolvated form. In a more preferred embodiment, the crystalline form A of the citrate salt of the compound of Formula (I) of the present invention is an anhydrous crystalline form.

Tartrate Salt of the Compound of Formula (I)

It is an object of the present invention to provide a tartrate salt of the compound of Formula (I) as shown below:

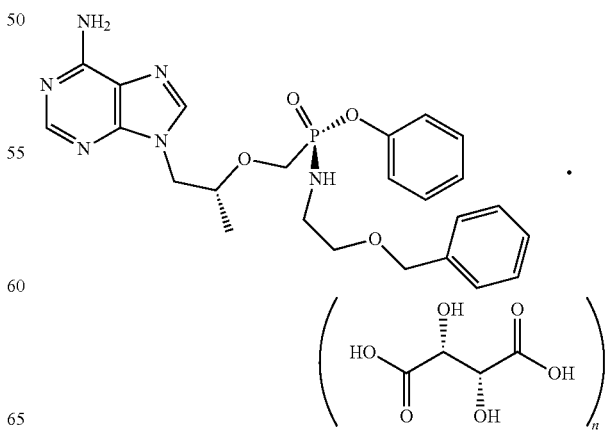

wherein n is 1 or ½, preferably 1. In other words, in the tartrate salt of the compound of Formula (I), the molar ratio of the compound of Formula (I) to tartaric acid is 1:1 or 1:½, preferably 1:1.

According to an embodiment, the present invention provides crystalline form A of the tartrate salt of the compound of Formula (I), wherein the molar ratio of the compound of Formula (I) to tartaric acid is 1:1. The crystalline form A of the tartrate salt of the compound of Formula (I) has an XRPD pattern comprising characteristic peaks at diffraction angles (2θ) of 16.9±0.2°, 17.2±0.2°, 18.7±0.2°, 19.2±0.2°, and 21.9±0.2°. In a preferred embodiment, the crystalline form A of the tartrate salt of the compound of Formula (I) has an XRPD pattern comprising characteristic peaks at diffraction angles (2θ) of 4.5±0.2°, 6.8±0.2°, 10.9±0.2°, 16.9±0.2°, 17.2±0.2°, 17.9±0.2°, 18.7±0.2°, 19.1±0.2°, 19.2±0.2°, and 21.9±0.2°. In a more preferred embodiment, the crystalline form A of the tartrate salt of the compound of Formula (I) has an XRPD pattern comprising characteristic peaks at diffraction angles (2θ) of 3.9±0.2°, 4.5±0.2°, 6.8±0.2°, 7.3±0.2°, 9.1±0.2°, 10.2±0.2°, 10.9±0.2°, 14.2±0.2°, 16.4±0.2°, 16.9±0.2°, 17.2±0.2°, 17.9±0.2°, 18.7±0.2°, 19.1±0.2°, 19.2±0.2°, 21.9±0.2°, 22.8±0.2°, 25.7±0.2°, and 27.6±0.2°. In a particularly preferred embodiment, the crystalline form A of the tartrate salt of the compound of Formula (I) has an XRPD pattern comprising peaks at the following diffraction angles (2θ):

| 2θ (°) ± 0.2° | Intensity % |
| --- | --- |
| 3.9 | 16.7 |
| 4.5 | 26.5 |
| 6.8 | 22.5 |
| 7.3 | 11.5 |
| 9.1 | 10.6 |
| 10.2 | 11.0 |
| 10.9 | 18.8 |
| 11.5 | 7.1 |
| 13.7 | 6.4 |
| 14.2 | 10.3 |
| 16.4 | 10.6 |
| 16.9 | 100.0 |
| 17.2 | 45.3 |
| 17.9 | 21.2 |
| 18.7 | 55.4 |
| 19.1 | 30.3 |
| 19.2 | 38.9 |
| 21.9 | 34.7 |
| 22.8 | 8.9 |
| 25.7 | 16.6 |
| 27.6 | 8.9 |

Figure 9:
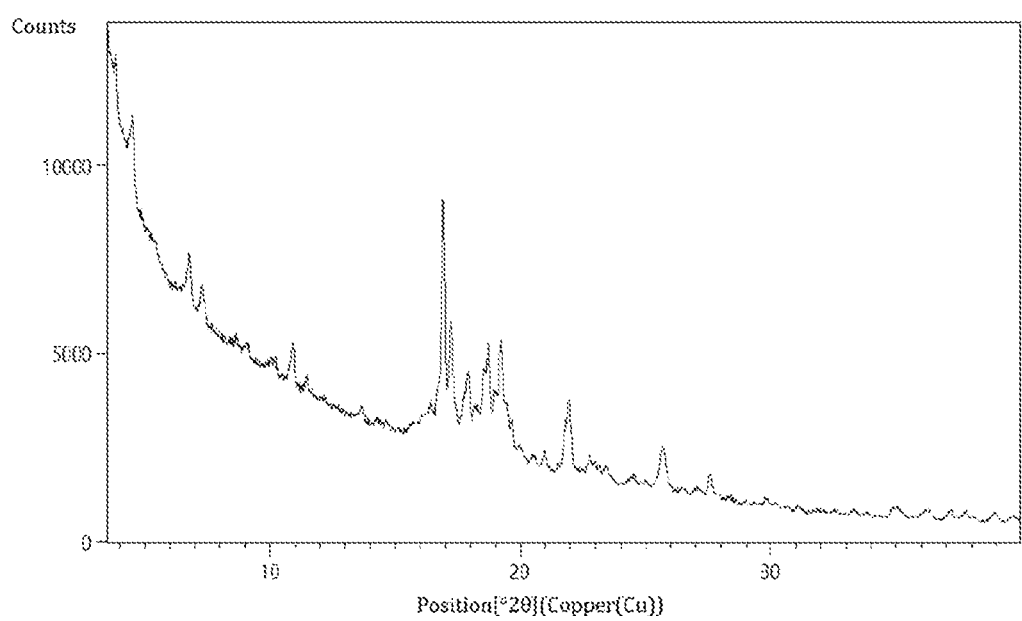
FIG. 9 shows an XRPD pattern of crystalline form A of the tartrate salt of the compound of Formula (I).

In a particularly preferred embodiment, the crystalline form A of the tartrate salt of the compound of Formula (I) has an XRPD pattern comprising peaks at diffraction angles (2θ) essentially the same as shown in FIG. 9. In a particularly preferred embodiment, the crystalline form A of the tartrate salt of the compound of Formula (I) has XRPD peak positions essentially the same as shown in FIG. 9.

According to another embodiment, the present invention provides crystalline form B of the tartrate salt of the compound of Formula (I), wherein the molar ratio of the compound of Formula (I) to tartaric acid is 1:1. The crystalline form B of the tartrate salt of the compound of Formula (I) has an XRPD pattern comprising characteristic peaks at diffraction angles (2θ) of 7.3±0.2°, 17.2±0.2°, 17.8±0.2°, 18.2±0.2°, and 19.2±0.2°. In a preferred embodiment, the crystalline form B of the tartrate salt of the compound of Formula (I) has an XRPD pattern comprising characteristic peaks at diffraction angles (2θ) of at 7.3±0.2°, 17.2±0.2°, 17.8±0.2°, 18.2±0.2°, 18.5±0.2°, 18.8±0.2°, 19.2±0.2°, 19.6±0.2°, 20.0±0.2°, and 21.9±0.2°. In a more preferred embodiment, the crystalline form B of the tartrate salt of the compound of Formula (I) has an XRPD pattern comprising characteristic peaks at diffraction angles (2θ) of 3.9±0.2°, 7.3±0.2°, 7.8±0.2°, 8.4±0.2°, 9.8±0.2°, 14.6±0.2°, 15.6±0.2°, 17.2±0.2°, 17.5±0.2°, 17.8±0.2°, 18.2±0.2°, 18.5±0.2°, 18.8±0.2°, 19.2±0.2°, 19.6±0.2°, 20.0±0.2°, 20.6±0.2°, 21.9±0.2°, 22.3±0.2°, and 23.7±0.2°. In a particularly preferred embodiment, the crystalline form B of the tartrate salt of the compound of Formula (I) has an XRPD pattern comprising peaks at the following diffraction angles (2θ):

| 2θ (°) ± 0.2° | Intensity % |
| --- | --- |
| 3.9 | 20.0 |
| 7.3 | 100.0 |
| 7.8 | 29.9 |
| 8.4 | 18.5 |
| 8.8 | 15.3 |
| 9.8 | 21.1 |
| 14.6 | 35.4 |
| 15.6 | 20.0 |
| 16.2 | 13.3 |
| 17.2 | 87.6 |
| 17.5 | 44.4 |
| 17.8 | 65.8 |
| 18.2 | 65.3 |
| 18.5 | 63.1 |
| 18.8 | 63.5 |
| 19.2 | 87.8 |
| 19.6 | 63.7 |
| 20.0 | 54.6 |
| 20.6 | 24.4 |
| 21.9 | 46.4 |
| 22.3 | 21.1 |
| 23.7 | 23.1 |
| 25.1 | 11.4 |
| 25.8 | 10.2 |
| 28.3 | 9.9 |
| 29.7 | 10.9 |

Figure 10:
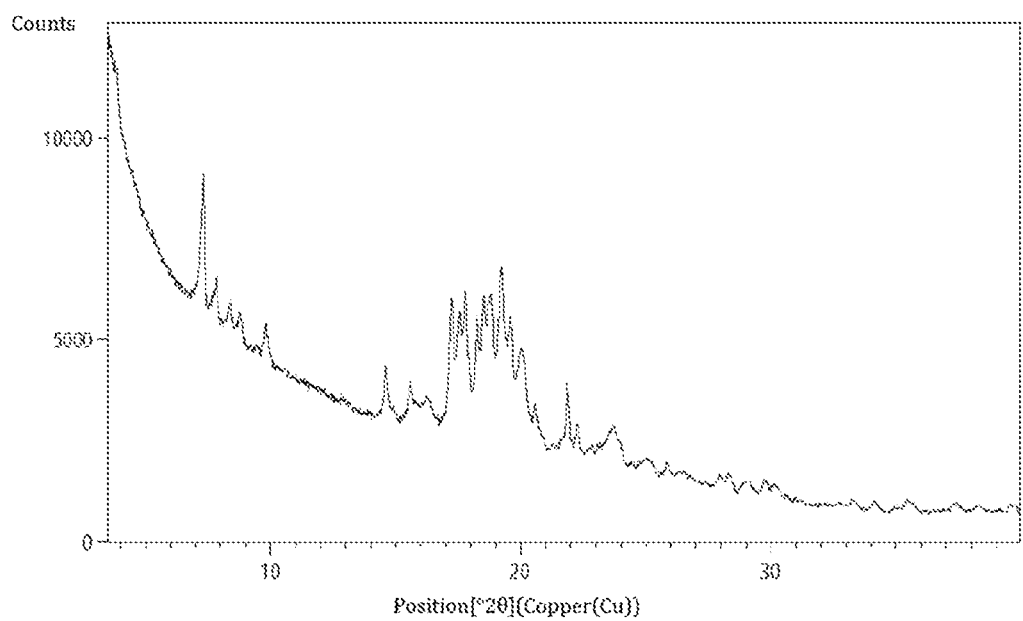
FIG. 10 shows an XRPD pattern of crystalline form B of the tartrate salt of the compound of Formula (I).

In a particularly preferred embodiment, the crystalline form B of the tartrate salt of the compound of Formula (I) has an XRPD pattern comprising peaks at diffraction angles (2θ) essentially the same as shown in FIG. 10. In a particularly preferred embodiment, the crystalline form B of the tartrate salt of the compound of Formula (I) has XRPD peak positions essentially the same as shown in FIG. 10.

Figure 11:
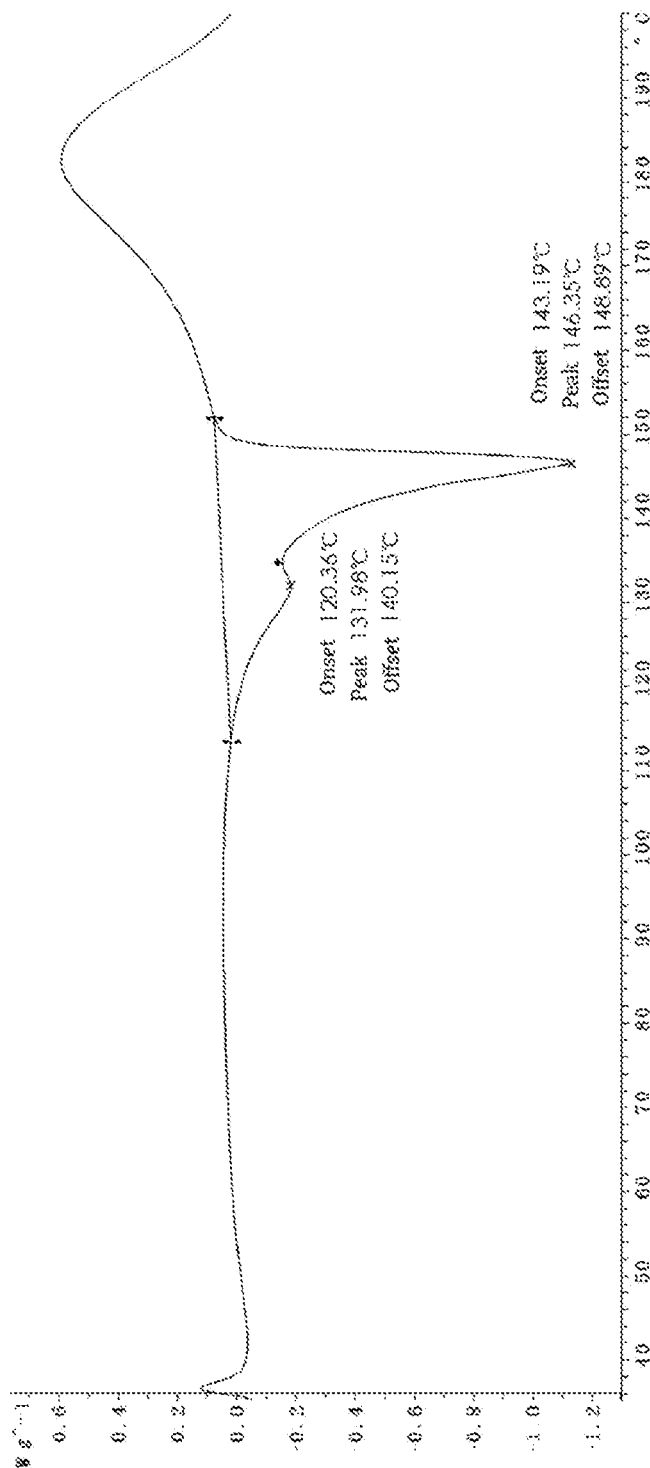
FIG. 11 shows a DSC graph of crystalline form B of the tartrate salt of the compound of Formula (I).
Figure 12:
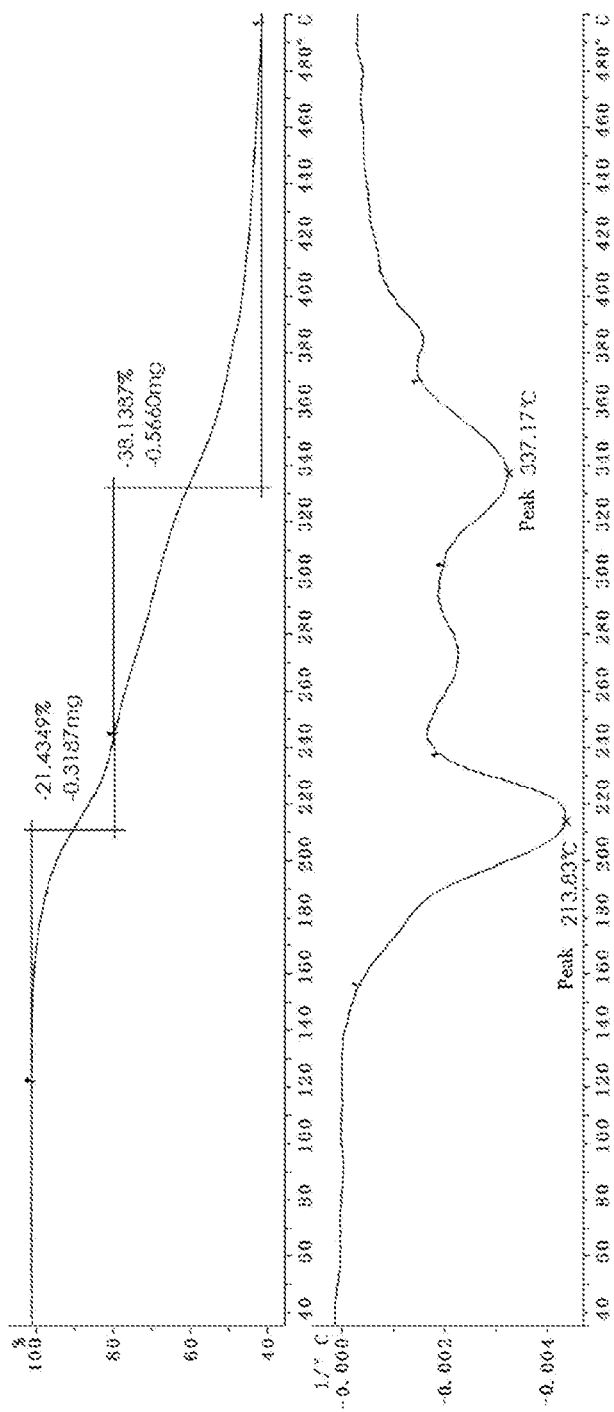
FIG. 12 shows a TGA graph of crystalline form B of the tartrate salt of the compound of Formula (I).

In a preferred embodiment, the crystalline form B of the tartrate salt of the compound of Formula (I) of the invention has a DSC graph comprising a characteristic peak at about 143±5° C. (the onset temperature), preferably about 143±2° C. (the onset temperature), and more preferably about 143±0.2° C. (the onset temperature). In a further preferred embodiment, the crystalline form B of the tartrate salt of the compound of Formula (I) of the invention has a DSC graph comprising a characteristic peak at a temperature essentially the same as shown in FIG. 11. In a particularly preferred embodiment, the characteristic peak position in the DSC graph of the crystalline form B of the tartrate salt of the compound of Formula (I) is essentially the same as shown in FIG. 11.

In a particularly preferred embodiment, the crystalline form B of the tartrate salt of the compound of Formula (I) of the present invention is in an unsolvated form. In a more preferred embodiment, the crystalline form B of the tartrate salt of the compound of Formula (I) of the present invention is an anhydrous crystalline form.

Phosphate Salt of the Compound of Formula (I)

It is an object of the present invention to provide a phosphate salt of the compound of Formula (I) as shown below:

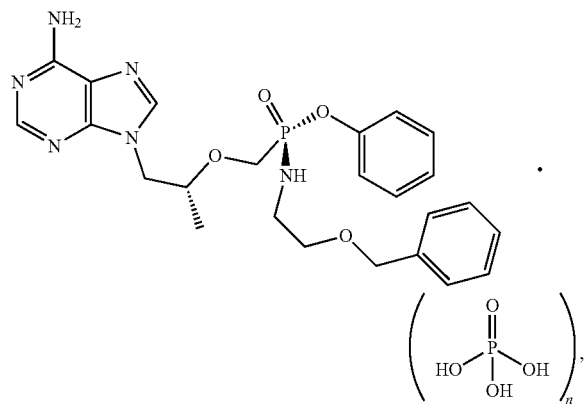

wherein n is 1 or ½ or ⅓, preferably 1. In other words, in the phosphate salt of the compounds of Formula (I), the molar ratio of the compound of Formula (I) to phosphoric acid is 1:1 or 1:½ or 1:⅓, preferably 1:1.

According to an embodiment, the present invention provides crystalline form A of the phosphate salt of the compound of Formula (I). The crystalline form A of the phosphate salt of the compound of Formula (I) has an XRPD pattern comprising characteristic peaks at diffraction angles (2θ) of 5.3±0.2°, 14.5±0.2°, 17.3±0.2°, 18.6±0.2°, and 19.5±0.2°. In a preferred embodiment, the crystalline form A of the phosphate salt of the compound of Formula (I) has an XRPD pattern comprising characteristic peaks at diffraction angles (2θ) of 5.3±0.2°, 7.9±0.2°, 14.5±0.2°, 16.3±0.2°, 17.3±0.2°, 18.6±0.2°, 19.5±0.2°, 20.4±0.2°, 20.7±0.2°, and 23.1±0.2°. In a particularly preferred embodiment, the crystalline form A of the phosphate salt of the compound of Formula (I) has an XRPD pattern comprising peaks at the following diffraction angles (2θ):

| 2θ (°) ± 0.2° | Intensity % |
|---|---|
| 5.3 | 100.0 |
| 7.9 | 13.0 |
| 14.5 | 26.0 |
| 16.3 | 16.0 |
| 17.3 | 30.3 |
| 18.6 | 19.4 |
| 19.5 | 41.7 |
| 20.4 | 16.5 |
| 20.7 | 11.9 |
| 23.1 | 10.6 |
| 27.0 | 6.9 |
| 32.5 | 7.5 |

Figure 13:
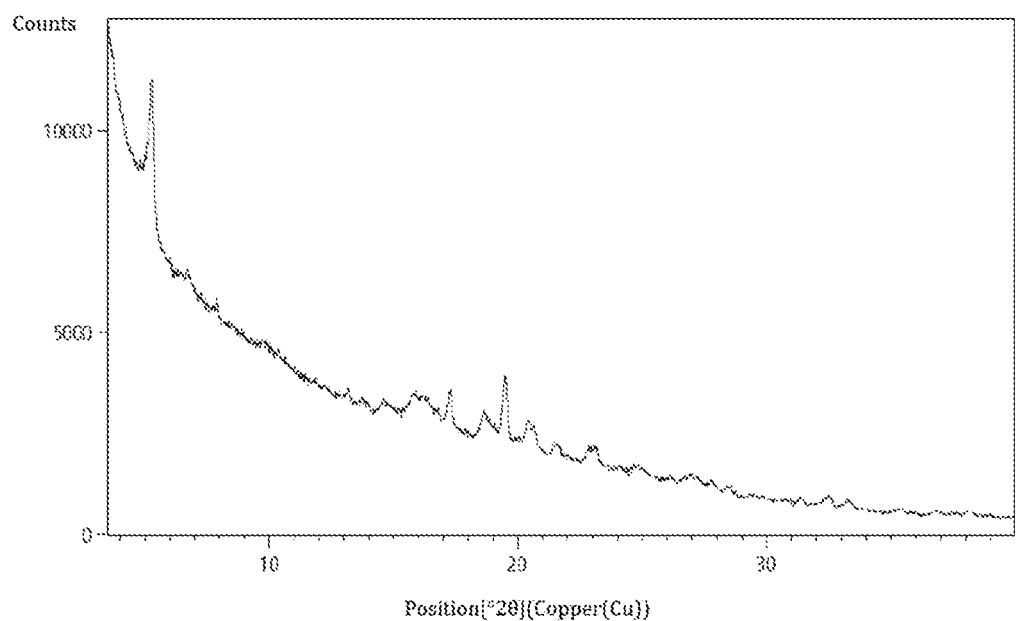
FIG. 13 shows an XRPD pattern of crystalline form A of the phosphate salt of the compound of Formula (I).

In a particularly preferred embodiment, the crystalline form A of the phosphate salt of the compound of Formula (I) has an XRPD pattern comprising peaks at diffraction angles (2θ) essentially the same as shown in FIG. 13. In a particularly preferred embodiment, the crystalline form A of the phosphate salt of the compound of Formula (I) has XRPD peak positions essentially the same as shown in FIG. 13.

Figure 14:
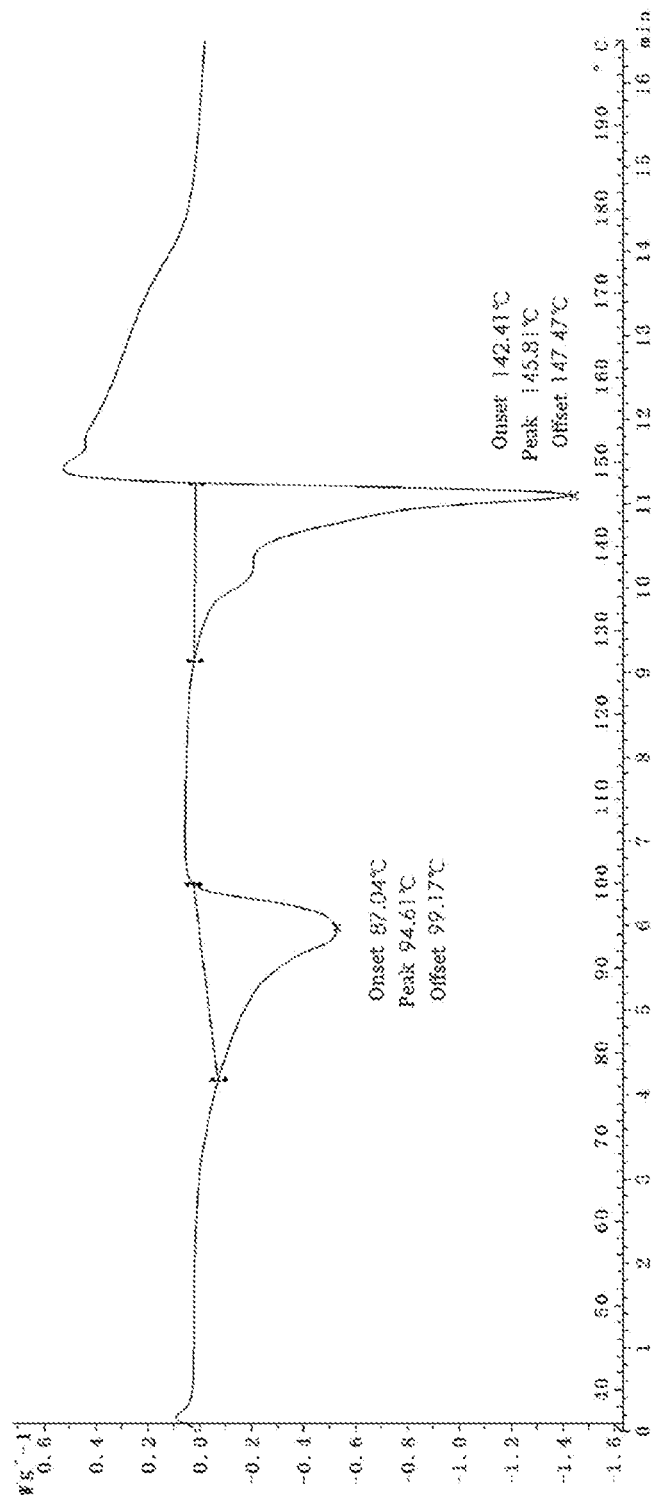
FIG. 14 shows a DSC graph of crystalline form A of the phosphate salt of the compound of Formula (I).
Figure 15:
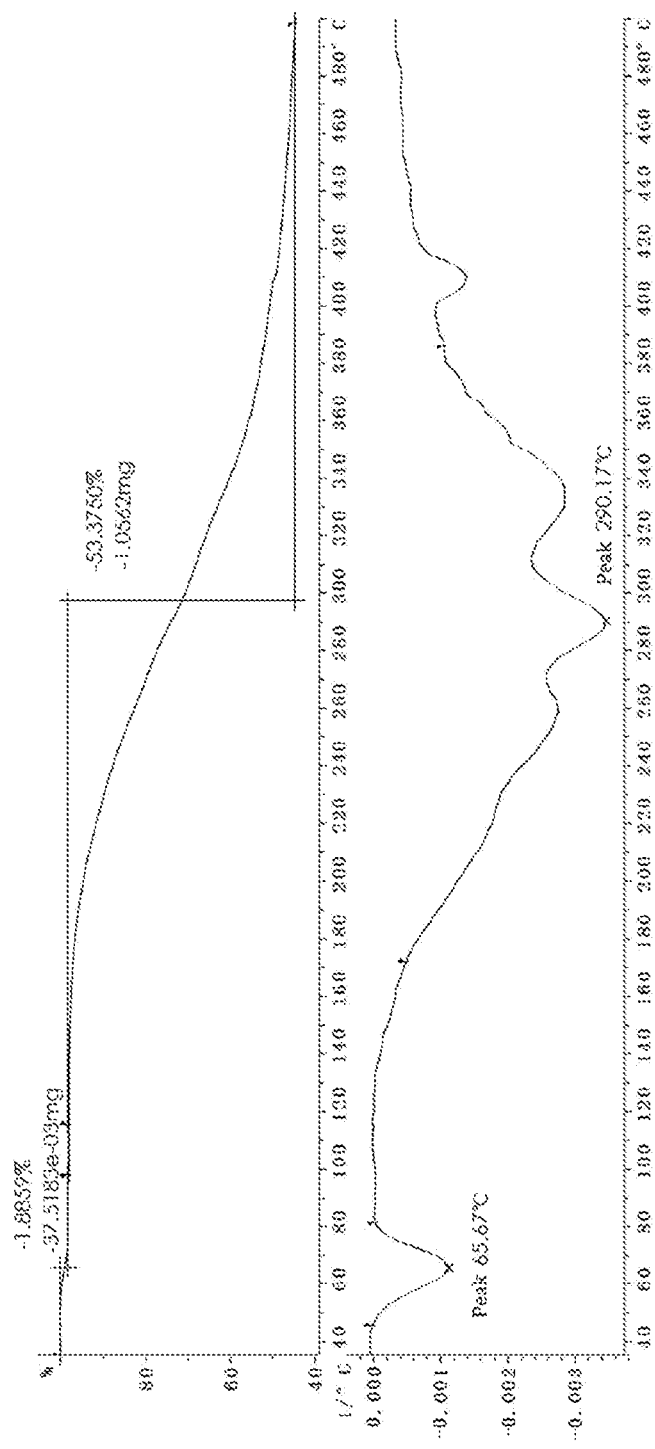
FIG. 15 shows a TGA graph of crystalline form A of the phosphate salt of the compound of Formula (I).

In a preferred embodiment, the crystalline form A of the phosphate salt of the compound of Formula (I) of the invention has a DSC graph comprising a characteristic peak at about 142±5° C., preferably about 142±2° C., and more preferably about 142±0.2° C. In a further preferred embodiment, the crystalline form A of the phosphate salt of the compound of Formula (I) of the invention has a DSC graph comprising a characteristic peak at a temperature essentially the same as shown in FIG. 14. In a particularly preferred embodiment, the characteristic peak position in the DSC graph of the crystalline form A of the phosphate salt of the compound of Formula (I) is essentially the same as shown in FIG. 14.

In a particularly preferred embodiment, the crystalline form A of the phosphate salt of the compound of Formula (I) of the present invention is in an unsolvated form. In a more preferred embodiment, the crystalline form A of the phosphate salt of the compound of Formula (I) of the present invention is an anhydrous crystalline form.

According to another embodiment, the present invention provides crystalline form B of the phosphate salt of the compound of Formula (I). The crystalline form B of the phosphate salt of the compound of Formula (I) has an XRPD pattern comprising characteristic peaks at diffraction angles (2θ) of 7.9±0.2°, 15.9±0.2°, 16.3±0.2°, 18.8±0.2°, and 24.2±0.2°. In a preferred embodiment, the crystalline form B of the phosphate salt of the compound of Formula (I) has an XRPD pattern comprising characteristic peaks at diffraction angles (2θ) of 7.9±0.2°, 10.4±0.2°, 12.2±0.2°, 15.9±0.2°, 16.3±0.2°, 18.8±0.2°, 19.4±0.2°, 20.0±0.2°, 24.2±0.2°, and 24.7±0.2°. In a particularly preferred embodiment, the crystalline form B of the phosphate salt of the compound of Formula (I) has an XRPD pattern comprising peaks at the following diffraction angles (2θ):

| 2θ (°) ± 0.2° | Intensity % |
|---|---|
| 7.9 | 84.2 |
| 10.4 | 21.9 |
| 11.8 | 12.7 |
| 12.2 | 18.6 |
| 15.9 | 69.1 |
| 16.3 | 50.3 |
| 18.8 | 100.0 |
| 19.4 | 24.9 |
| 20.0 | 21.0 |
| 21.9 | 13.3 |
| 23.1 | 10.1 |
| 24.2 | 36.1 |
| 24.7 | 20.5 |
| 26.2 | 13.9 |
| 27.8 | 15.0 |

Figure 16:
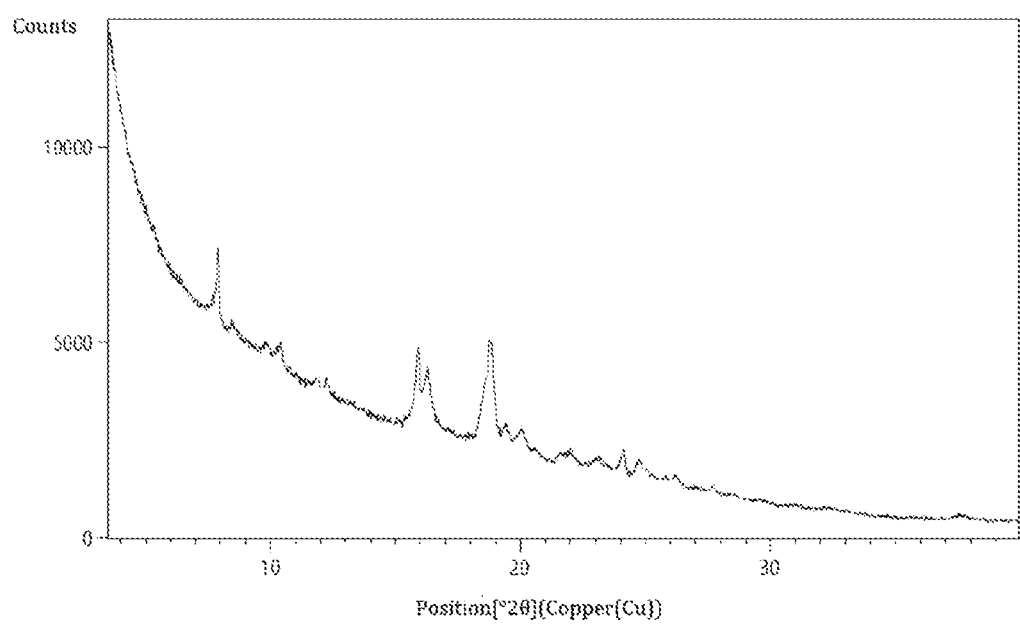
FIG. 16 shows an XRPD pattern of crystalline form B of the phosphate salt of the compound of Formula (I).
Figure 17:
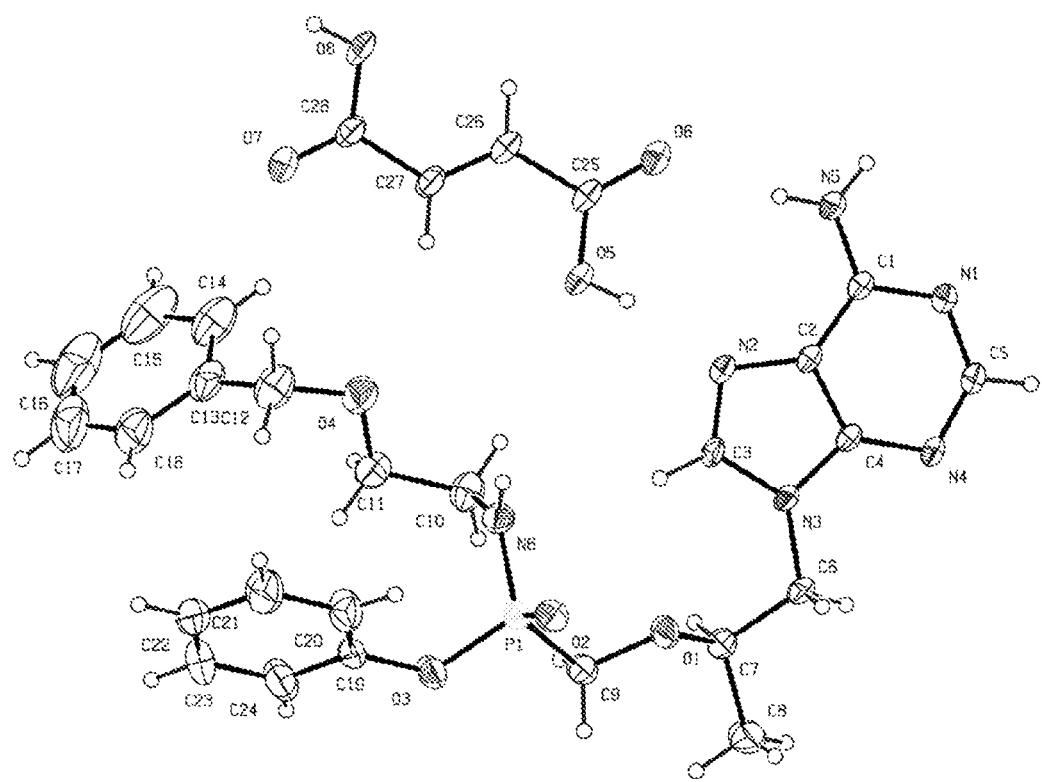
FIG. 17 shows a graph of the stereochemical structure of the single crystal molecule of crystalline form A of the fumarate salt of the compound of Formula (I).

In a particularly preferred embodiment, the crystalline form B of the phosphate salt of the compound of Formula (I) has an XRPD pattern comprising peaks at diffraction angles (2θ) essentially the same as shown in FIG. 16. In a particularly preferred embodiment, the crystalline form B of the phosphate salt of the compound of Formula (I) has XRPD peak positions essentially the same as shown in FIG. 16.

Another object of the present invention is to provide a method for preparing the salt (including, but not limited to, the fumarate salt, the citrate salt, the tartrate salt and the hydrochloride salt) of the compound of Formula (I) described above and various crystalline forms thereof. The method comprises reacting the compound of Formula (I) in any solid form with an inorganic acid or an organic acid, precipitating solid, and subsequently separating and drying the precipitated solid. The method for precipitating solid includes, but is not limited to: a gas-solid permeation method, an anti-solvent addition method, a room temperature suspension stirring method, a high temperature suspension stirring method, a gas-liquid permeation method, a room temperature slow volatilization method, a slow cooling method, a reverse anti-solvent addition method and the like. That is to say, the various crystalline forms of the fumarate salt, citrate salt, tartrate salt and hydrochloride salt of the compound of Formula (I) of the present invention described above can be prepared by a gas-solid permeation method, an anti-solvent addition method, a room temperature suspension stirring method, a high temperature suspension stirring method, a gas-liquid permeation method, a room temperature slow volatilization method, a slow cooling method, or a reverse anti-solvent addition method.

According to some embodiments of the present invention, a crystalline form is prepared by a gas-solid permeation method, comprising placing a first vessel containing a salt of the compound of Formula (I) in a second vessel containing a solvent, wherein the salt of the compound of Formula (I) in a solid form is not in direct contact with the solvent, sealing the second vessel, and obtaining the crystalline form upon placement. In some embodiments where the crystalline form is prepared by the gas-solid permeation method, the solvent includes, but is not limited to, inorganic solvents (e.g., water) and organic solvents, such as alcohols, amides, sulfones, ketones, hydrocarbons (including alkanes, halogenated alkanes, alkenes, alkynes and aromatic hydrocarbons), ethers (including chain ethers and cyclic ethers (such as furans (including tetrahydrofurans) and dioxanes)), nitriles and esters, such as methanol, ethanol, isopropanol, trichloromethane, acetone, isopropyl acetate, methyl tert-butyl ether, tetrahydrofuran, dioxane, acetonitrile, dichloromethane, N,N-dimethylformamide, dimethylsulfoxide, ethyl acetate, and the like. In some embodiments where the crystalline form is prepared by the gas-solid permeation method, the weight/volume ratio (mg/mL) of the salt of the compound of Formula (I) to the solvent is about (1-20):1, preferably (2-10):1. In some embodiments where the crystalline form is prepared by the gas-solid permeation method, crystal precipitation upon placement comprises crystal precipitation by standing or crystal precipitation by stirring, preferably by standing.

According to some embodiments of the present invention, a crystalline form is prepared by an anti-solvent addition method, comprising, but not limited to, dissolving a salt of the compound of Formula (I) in a good solvent to form a clear solution (the solution may be filtered as needed to provide a clear solution), then adding an anti-solvent thereto, and stirring (the stirring may be carried out at room temperature or under cooling (e.g., cooling to 0-20° C., preferably 0-10° C., such as 0° C., 5° C., or 10° C.)) to allow the precipitation of the crystalline form, or leaving the solution to stand (e.g., at room temperature) (preferably, slowly volatilizing the solvents at the same time) to allow the precipitation of the crystalline form. In some embodiments where the crystalline form is prepared by the anti-solvent additions method, the good solvent includes, but is not limited to, organic solvents, such as alcohols, ketones, nitriles, hydrocarbons (selected from halogenated alkanes and aromatic hydrocarbons), ethers (including chain ethers and cyclic ethers (such as furans (including tetrahydrofurans) and dioxanes)), sulfones, esters, amides and organic acids, such as methanol, ethanol, acetone, acetonitrile, tetrahydrofuran, dimethyl sulfoxide, N,N-dimethylacetamide, N-methylpyrrolidone, methyl ethyl ketone, ethyl acetate, 2-methyltetrahydrofuran, cyclopentyl methyl ether, anisole, toluene, dichloromethane and the like. In some embodiments where the crystalline form is prepared by the anti-solvent additions method, the anti-solvent includes, but is not limited to, inorganic solvents (e.g., water) and organic solvents (e.g., hydrocarbons (selected from alkanes, alkenes and alkynes), such as n-hexane, n-heptane, cyclohexane, and the like). In some embodiments where the crystalline form is prepared by the anti-solvent additions method, the volume ratio of the good solvent to the anti-solvent is 1:(1-60), preferably 1:(1-40). In some embodiments, the weight/volume ratio (mg/mL) of the salt of the compound of Formula (I) to the good solvent is (1-80): 1, preferably (1-40): 1.

In some embodiments where the solid are precipitated by the anti-solvent addition method, various crystalline forms of the fumarate salt, citrate salt, tartrate salt or phosphate salt of the compound of Formula (I) are prepared by the following: reacting the compound of Formula (I) in any solid form (e.g. crystalline forms or amorphous form) with fumaric acid, citric acid, tartaric acid or phosphoric acid in a good solvent, then adding an anti-solvent thereto after the reaction is completed, stirring (the stirring may be carried out at room temperature or under cooling (e.g., cooling to 0-20° C., preferably 0-10° C., such as 0° C., 5° C., or 10° C.)) to allow the precipitation of the crystalline form, or leaving the solution to stand (e.g., at room temperature) (preferably, slowly volatilizing the solvents at the same time) to allow the precipitation of the crystalline form, isolating the precipitated crystalline form, and drying. The volume ratio of the good solvent to the anti-solvent is 1:(1-60), preferably 1:(1-40). The weight/volume ratio (mg/mL) of the salt of the compound of Formula (I) to the good solvent is (1-80):1, preferably (10-40):1.

According to some embodiments of the present invention, a crystalline form is prepared by a room temperature suspension stirring method, comprising, but not limited to, adding a salt the compound of Formula (I) to a solvent to give a suspension, stirring the suspension at room temperature, followed by isolation to afford the crystalline form. In some embodiments where the crystalline form is prepared by the room temperature suspension stirring method, the solvent includes, but is not limited to, inorganic solvents (e.g., water) and organic solvents (e.g., alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), esters, nitriles, amides and organic acids, such as methyl tert-butyl ether, isopropyl alcohol, isobutyl acetate, methanol, acetone, tetrahydrofuran, acetonitrile, dimethylsulfoxide, 2-methyltetrahydrofuran, dichloromethane, ethyl acetate, toluene and the like), or a mixed solvent of two or more selected from the above solvents. In some embodiments where the crystalline form is prepared by the room temperature suspension stirring method, the weight/volume ratio (mg/mL) of the salt of the compound of Formula (I) to the solvent is (1-80):1, preferably (1-50):1.

According to some embodiments of the present invention, a crystalline form is prepared by a high temperature suspension stirring method, comprising, but not limited to, adding a salt of the compound of Formula (I) to a solvent to give a suspension, stirring the suspension under heating (e.g., heated to 40-100° C., preferably 40-80° C., such as 45° C., 50° C., 55° C., 60° C., 65° C. or 70° C.), followed by isolation to afford the crystalline form. In some embodiments where the crystalline form is prepared by the high temperature suspension stirring method, the solvent includes, but is not limited to, inorganic solvents (e.g., water) and organic solvents (e.g., alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), esters, nitriles, sulfones, amides, and nitrogen-containing heterocycles, such as methyl ethyl ketone, isobutyl alcohol, isobutyl acetate, methanol, acetone, tetrahydrofuran, acetonitrile, dimethyl sulfoxide, 2-methyltetrahydrofuran, trichloromethane, ethyl acetate, toluene, n-hexane, and the like), or a mixed solvent of two or more selected from the above solvents. In some embodiments where the crystalline form is prepared by the high temperature suspension stirring method, the weight/volume ratio (mg/mL) of the salt of the compound of Formula (I) to the solvent is (1-80):1, preferably (5-60):1.

According to some embodiments of the present invention, a crystalline form is prepared by a gas-liquid permeation method, comprising dissolving a salt of the compound of Formula (I) in a good solvent in a first vessel to form a clear solution (the solution may be filtered as needed to provide a clear solution), adding an anti-solvent to a second vessel, placing the open first vessel in the second vessel, sealing the second vessel and allowing it to stand, and filtering the precipitated solid to afford the crystalline form. In some embodiments where the crystalline form is prepared by the gas-liquid permeation method, the good solvent includes, but is not limited to, organic solvents, such as hydrocarbons (selected from halogenated alkanes and aromatic hydrocarbons), alcohols, ketones, ethers (including chain ethers and cyclic ethers (such as furans (including tetrahydrofurans) and dioxanes), esters, nitriles, sulfones, amides, nitrogen-containing heterocycles, and the like, e.g., methanol, ethanol, acetone, tetrahydrofuran, acetonitrile, dimethylsulfoxide, isopropanol, methyl isobutyl ketone, isopropyl acetate, methyl tert-butyl ether, 1,4-dioxane, anisole, cyclopentyl methyl ether, toluene, trichloromethane, or a mixed solvent formed by two or more of the above solvents. In some embodiments where the crystalline form is prepared by the gas-liquid permeation method, the anti-solvent includes, but is not limited to, inorganic solvents (e.g., water) and organic solvents (e.g., hydrocarbons (selected from alkanes, alkenes, and alkynes), such as n-hexane, n-heptane, cyclohexane, and the like), or a mixed solvent formed by two or more of the above solvents. In some embodiments where the crystalline form is prepared by the gas-liquid permeation method, the weight/volume ratio (mg/mL) of the salt of the compound of Formula (I) to the good solvent is about (1-80):1, preferably (10-60):1. In some embodiments, the volume ratio of the good solvent to the anti-solvent is 1:(1-20), preferably 1:(1-10). In some embodiments, the sealing and standing of the second vessel can be carried out at room temperature.

According to some embodiments of the present invention, a crystalline form is prepared by a room temperature slow volatilization method, comprising dissolving a salt of the compound of Formula (I) in a solvent in a vessel to form a clear solution (the solution may be filtered as needed to provide a clear solution), sealing (e.g., with parafilm) the vessel while retaining a small hole or slit in the seal, allowing the clear solution to stand, and volatilizing the solvent, to afford the crystalline form. In some embodiments where the crystalline form is prepared by the room temperature slow volatilization method, the solvent includes, but is not limited to, inorganic solvents (e.g., water) and organic solvents (e.g., alcohols, amides, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), ketones, nitriles or esters, such as isopropyl alcohol, methyl ethyl ketone, isopropyl acetate, 2-methyl-tetrahydrofuran, cyclopentyl methyl ether, methanol, acetone, acetonitrile, ethyl acetate, n-hexane, tetrahydrofuran, dichloromethane and the like), or a mixed solvent formed by two or more of the above solvents. In some embodiments where the crystalline form is prepared by the room temperature slow volatilization method, the weight/volume ratio (mg/mL) of the salt of the compound of Formula (I) to the solvent is (1-50):1, preferably (1-30):1. In some embodiments, the standing can be carried out at room temperature.

In some embodiments where the solid are precipitated by the room temperature slow volatilization method, various crystalline forms of the fumarate salt, citrate salt, tartrate salt, or phosphate salt of the compound of Formula (I) are prepared by the following: dissolving the compound of Formula (I) in any solid form (e.g. crystalline forms or amorphous form) and reacting with fumaric acid, citric acid, tartaric acid or phosphoric acid in a solvent, slowly volatilizing at room temperature after the reaction is completed to allow the precipitation of the crystalline form, isolating the precipitated crystalline form, and drying. The weight/volume ratio (mg/mL) of the salt of the compound of Formula (I) to the solvent is (1-50):1, preferably (1-30):1.

According to some embodiments of the present invention, a crystalline form is prepared by a slow cooling method, comprising adding a salt of the compound of Formula (I) to a solvent, heating and stirring to dissolve the compound, allowing the resulting clear solution (the solution may be filtered as needed to provide a clear solution) to stand, and slowly cooling to afford the crystalline form. In some embodiments where the crystalline form is prepared by the slow cooling method, the solvent includes, but is not limited to, inorganic solvents (e.g., water) and organic solvents (e.g., alcohols, ketones, hydrocarbons (including alkanes, halogenated alkanes, alkenes, alkynes, and aromatic hydrocarbons), ethers (including chain ethers and cyclic ethers (such as furans (including tetrahydrofurans) and dioxanes)), nitriles, amides and esters, such as methyl isobutyl ketone, isobutyl alcohol, isobutyl acetate, methanol, tetrahydrofuran, ethanol, 2-methyltetrahydrofuran, n-hexane, and the like), or a mixed solvent formed by two or more of the above solvents. In some embodiments where the crystalline form is prepared by the slow cooling method, the slow cooling refers to, for example, a temperature-reducing rate of 0.1-0.5° C./minute, e.g., 0.1-0.3° C./minute, and preferably 0.1° C./minute. In some embodiments, the heating temperature is 30-80° C., preferably 40-70° C., e.g., 45° C., 50° C., 55° C., or 60° C. In some embodiments, the temperature at the end of the cooling is room temperature or 0-10° C., e.g., 3° C., 5° C., or 7° C. In some embodiments where the crystalline form is prepared by the slow cooling method, the weight/volume ratio (mg/mL) of the salt of the compound of Formula (I) to the solvent is (2-100):1, preferably (10-80):1.

According to some embodiments of the present invention, a crystalline form is prepared by a reverse anti-solvent addition method, comprising, but not limited to, dissolving a salt of the compound of Formula (I) in a good solvent to form a clear solution (the solution may be filtered as needed to provide a clear solution), then adding the clear solution to an anti-solvent, and stirring (the stirring may be carried out at room temperature or under heating (e.g., heating to 30-100° C., preferably 30-80° C., and more preferably 35-65° C., for example, 45° C., 50° C., 55° C. or 60° C.) to allow the precipitation of the crystalline form, or leaving the solution to stand (e.g., at room temperature) (preferably, slowly volatilizing the solvents at the same time) to allow the precipitation of the crystalline form. In some embodiments where the crystalline form is prepared by the reverse anti-solvent addition method, the good solvent includes, but is not limited to, organic solvents, such as alcohols, ketones, hydrocarbons (selected from halogenated alkanes and aromatic hydrocarbons), ethers (including chain ethers and cyclic ethers (such as furans (including tetrahydrofurans) and dioxanes)), sulfones, amides and organic acids, such as N-methylpyrrolidone, ethanol, acetone, acetonitrile, tetrahydrofuran, dichloromethane, methyl isobutyl ketone, ethyl acetate, 2-methyltetrahydrofuran, toluene and the like. In some embodiments where the crystalline form is prepared by the reverse anti-solvent addition method, the anti-solvent includes, but is not limited to, inorganic solvents (e.g., water) and organic solvents (e.g., hydrocarbons (selected from alkanes, alkenes and alkynes), such as cyclohexane, n-hexane, n-heptane, and the like. In some embodiments where the crystalline form is prepared by the reverse anti-solvent addition method, the volume ratio of the good solvent to the anti-solvent is (1-20):1, preferably (1-10):1. In some embodiments, the weight/volume ratio (mg/mL) of the salt of the compound of Formula (I) to the good solvent is (1-80):1, preferably (1-50):1.

Pharmaceutical Composition and Use Thereof

Another object of the present invention is to provide a pharmaceutical composition comprising:

i) the salt of the compound of Formula (I) according to the invention, for example, the fumarate salt, citrate salt, tartrate salt or phosphate salt of the compound of Formula (I), in particular the fumarate salt, citrate salt, tartrate salt or phosphate salt of the compound of Formula (I) in a solid form, more particularly the crystalline forms of the fumarate salt of the compound of Formula (I), the crystalline forms of the citrate salt of the compound of Formula (I), the crystalline forms of the tartrate salt of the compound of Formula (I) or the crystalline forms of the phosphate salt of the compound of Formula (I), and more particularly crystalline form A, B or C of the fumarate salt of the compound of Formula (I), crystalline form A or B of the tartrate salt of the compound of Formula (I), crystalline form A of the citrate salt of the compound of Formula (I), or crystalline form A or B of the phosphate salt of the compound of Formula (I); and ii) one or more pharmaceutically acceptable carriers.

It is another object of the present invention to provide a method for treating viral infectious diseases such as hepatitis B in a subject, comprising administering to a subject in need thereof a therapeutically effective amount of the salt of the compound of Formula (I) according to the invention, for example, the fumarate salt, citrate salt, tartrate salt or phosphate salt of the compound of Formula (I), in particular the fumarate salt, citrate salt, tartrate salt or phosphate salt of the compound of Formula (I) in a solid form, more particularly the crystalline forms of the fumarate salt of the compound of Formula (I), the crystalline forms of the citrate salt of the compound of Formula (I), the crystalline forms of the tartrate salt of the compound of Formula (I) or the crystalline forms of the phosphate salt of the compound of Formula (I), and more particularly crystalline form A, B or C of the fumarate salt of the compound of Formula (I), crystalline form A or B of the tartrate salt of the compound of Formula (I), crystalline form A of the citrate salt of the compound of Formula (I), or crystalline form A or B of the phosphate salt of the compound of Formula (I), or any combination thereof.

It is another object of the present invention to provide the salt of the compound of Formula (I) according to the invention (for example, the fumarate salt, citrate salt, tartrate salt or phosphate salt of the compound of Formula (I), in particular the fumarate salt, citrate salt, tartrate salt or phosphate salt of the compound of Formula (I) in a solid form, more particularly the crystalline forms of the fumarate salt of the compound of Formula (I), the crystalline forms of the citrate salt of the compound of Formula (I), the crystalline forms of the tartrate salt of the compound of Formula (I) or the crystalline forms of the phosphate salt of the compound of Formula (I), and more particularly crystalline form A, B or C of the fumarate salt of the compound of Formula (I), crystalline form A or B of the tartrate salt of the compound of Formula (I), crystalline form A of the citrate salt of the compound of Formula (I), or crystalline form A or B of the phosphate salt of the compound of Formula (I), or any combination thereof) for use in the treatment of viral infectious diseases such as hepatitis B in a subject.

It is another object of the present invention to provide use of the salt of the compound of Formula (I) according to the invention (for example, the fumarate salt, citrate salt, tartrate salt or phosphate salt of the compound of Formula (I), in particular the fumarate salt, citrate salt, tartrate salt or phosphate salt of the compound of Formula (I) in a solid form, more particularly the crystalline forms of the fumarate salt of the compound of Formula (I), the crystalline forms of the citrate salt of the compound of Formula (I), the crystalline forms of the tartrate salt of the compound of Formula (I) or the crystalline forms of the phosphate salt of the compound of Formula (I), and more particularly crystalline form A, B or C of the fumarate salt of the compound of Formula (I), crystalline form A or B of the tartrate salt of the compound of Formula (I), crystalline form A of the citrate salt of the compound of Formula (I), or crystalline form A or B of the phosphate salt of the compound of Formula (I), or any combination thereof) in the manufacture of a medicament for treating viral infectious diseases such as hepatitis B in a subject.

As used herein, the term "pharmaceutically acceptable carrier" in the present invention refers to a diluent, auxiliary material, excipient, or vehicle with which a therapeutic is administered, and it is, within the scope of sound medical judgment, suitable for contact with the tissues of human beings and animals without excessive toxicity, irritation, allergic response, or other problem or complication, commensurate with a reasonable benefit/risk ratio.

The pharmaceutically acceptable carrier which can be employed in the pharmaceutical composition of the present invention includes, but is not limited to sterile liquids, such as water and oils, including those of petroleum, animal, vegetable or synthetic origin, such as peanut oil, soybean oil, mineral oil, sesame oil and the like. Water is an exemplary carrier when the pharmaceutical composition is administered intravenously. Physiological salines as well as aqueous dextrose and glycerol solutions can also be employed as liquid carriers, particularly for injectable solutions. Suitable pharmaceutical excipients include starch, glucose, lactose, sucrose, gelatin, maltose, chalk, silica gel, sodium stearate, glycerol monostearate, talc, sodium chloride, dried skim milk, glycerol, propylene glycol, water, ethanol and the like. The composition, if desired, can also contain minor amounts of wetting or emulsifying agents, or pH buffering agents. Oral formulations can include standard carriers such as pharmaceutical grades of mannitol, lactose, starch, magnesium stearate, sodium saccharine, cellulose, magnesium carbonate, etc. Examples of suitable pharmaceutical carriers are described in e.g. Remington's Pharmaceutical Sciences (1990).

The composition of the present invention can act systemically and/or topically. To this end, it can be administered through a suitable route, such as through injection, intravenous, intraarterial, subcutaneous, intraperitoneal, intramuscular, or transdermal administration, or administered via oral, buccal, nasal, transmucosal, topical, as an ophthalmic formulation, or via inhalation.

For these routes of administration, the composition of the present invention can be administered in a suitable dosage form.

The dosage form may be solid, semi-solid, liquid, or gas formulations, including, but not limited to, tablets, capsules, powders, granules, lozenges, hard candies, powders, sprays, creams, salves, suppositories, gels, pastes, lotions, ointments, aqueous suspensions, injectable solutions, suspensions, elixirs, and syrups.

The pharmaceutical composition of the present invention may be manufactured by any process well known in the art, e.g., by means of mixing, dissolving, granulating, dragee-making, levigating, emulsifying, lyophilizing processes, or the like.

As used herein, the term "therapeutically effective amount" refers to the amount of a compound being administered which will relieve to some extent one or more of the symptoms of the disorder being treated.

Dosage regimens may be adjusted to provide the optimum desired response. For example, a single bolus may be administered, several divided doses may be administered over time, or the dose may be proportionally reduced or increased as indicated by the exigencies of the therapeutic situation. It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the composition.

The amount of the compound of the present invention administered will be dependent on the subject being treated, the severity of the disorder or condition, the rate of administration, the disposition of the compound and the discretion of the prescribing physician. Generally, an effective dosage is in the range of about 0.0001 to about 50 mg per kg body weight per day, for example about 0.01 to about 10 mg/kg/day, in single or divided doses. For a 70 kg human, this would amount to about 0.007 mg to about 3500 mg/day, for example about 0.7 mg to about 700 mg/day. In some instances, dosage levels below the lower limit of the aforesaid range may be more than adequate, while in other cases, still larger doses may be employed without causing any harmful side effect, provided that such larger doses are first divided into several small doses for administration throughout the day.

The content or dosage of the compound of the present invention in the pharmaceutical composition is about 0.01 mg to about 1000 mg, suitably 0.1-500 mg, preferably 0.5-300 mg, more preferably 1-150 mg, particularly preferably 1-50 mg, e.g., 1.5 mg, 2 mg, 4 mg, 10 mg, and 25 mg, etc.

Unless otherwise indicated, the term "treating" or "treatment", as used herein, means reversing, alleviating, inhibiting the progress of, or preventing a disorder, condition, or disease to which such term applies, or one or more symptoms of such disorder, condition, or disease.

As used herein, the term "subject" includes a human or non-human animal. An exemplary human subject includes a human subject having a disease (such as one described herein) (referred to as a patient), or a normal subject. The term "non-human animal" as used herein includes all vertebrates, such as non-mammals (e.g., birds, amphibians, reptiles) and mammals, such as non-human primates, livestock and/or domesticated animals (such as sheep, dog, cat, cow, pig and the like).

EXAMPLES

The present invention is explained in more detail below with reference to the examples, which are only used to illustrate the technical solutions of the present invention, and are not intended to limit the scope thereof, and those skilled in the art may make some non-essential improvements and adjustments, which still fall within the scope of the present invention.

Test Instrument Information and Methods Used in the Experiments:

Method 1: X-Ray Powder Diffraction (XRPD)

Instrument Information:

Instrument name: Xpert$^3$ Powder

Anode material: Cu Pd

Sample supporter: transmisson film

Test Conditions:

| | | |
|---|---|---|
| Scan type: Absolute scan | Divergence slit: $\frac{1}{16}°$ | Anti-divergence slit: $\frac{1}{8}°$ |
| Slit width (mm): 7.5 | dark slide (mm): 20 | Scan mode: Continuous |
| Current (mA): 40 | Voltage (KV): 40 | Step size: 0.026° |
| Scan axis: Gonio | Sample injection stage: flats Sample Stage | |

Method 2: Differential Scanning calorimetry (DSC)

Instrument information: Mettler-Toledo DSC1

Test method: 35° C.-200° C.; 10K/min; and puncturing in the cap applied.

DSC data were collected on a Mettler-Toledo DSC1 differential scanning calorimeter.

Method 3: Thermogravimetric Analysis (TGA)

Instrument information: Mettler-Toledo TGA

Test method: 35° C.-500° C.; 10K/min.

TGA data were collected on a Mettler-Toledo TGA thermogravimetric analyzer.

Method 4: $^1$H-NMR $^1$H-NMR data were collected on a Bruker 400 MHz NMR instrument.

Method 5: Determination of cell parameters

The cell parameters were determined using an Xcalibur Eos diffractometer; and OLEX2 software was used to analyze single crystal structures.

Example 1

Preparation and Chiral Isolation of Racemates of (S)—P—((((R)-1-(6-amino-9H-purin-9-yl)propan-2-yl)oxy)methyl)-phenoxy-N-(2-(benzyloxy)ethyl)-phosphonamide (the Compound of Formula (I)) and (R)—P—((((R)-1-(6-amino-9H-purin-9-yl)propan-2-yl)oxy)methyl)-phenoxy-N-(2-(benzyloxy)ethyl)-phosphonamide (the Compound of Formula (II))

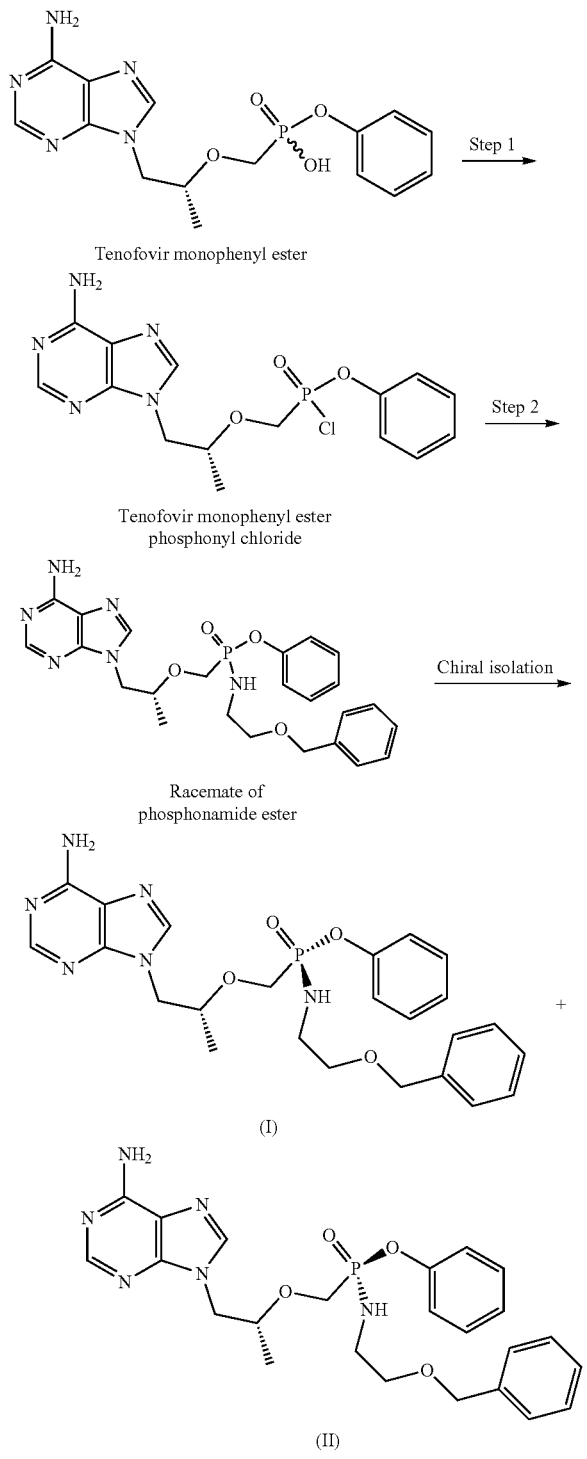

Step 1: Preparation of ((((R)-1-(6-amino-9H-purin-9-yl)-1-methyl-ethoxy)methyl)phenoxyphosphonyl Chloride (((1R)-2-(6-amino-9H-purin-9-yl)-1-methyl-ethoxy)methyl)phosphoric acid monophenyl ester (3.0 g, 8.3 mmol) was dissolved in acetonitrile (3 mL) at room temperature, and thionyl chloride (90 mL) was added. After the completion of the dropwise addition, the temperature of the reaction mixture was raised to 70° C. After reaction for 3 h, the reaction mixture was concentrated to afford the title compound (3.29 g), which was directly used in the subsequent reaction without purification.

ESI-MS (m/z): 378.1 $[M+H]^+$.

Step 2: Preparation of (2S)-((((1R)-2-(6-amino-9H-purin-9-yl)-1-methyl-ethoxy)methyl-phenoxy-phosphoryl)amino-3-(2-methylbenzyloxy)-propane ((((R)-1-(6-amino-9H-purin-9-yl)-1-methyl-ethoxy)methyl)phenoxyphosphonyl chloride (3.29 g, 8.3 mmol) was dissolved in dry dichloromethane (66 mL) at room temperature. The temperature of the reaction mixture was lowered to −20° C. 2-(benzyloxy)ethylamine (1.9 g, 12.3 mmol) was added, and triethylamine (9.6 mL) was added dropwise. After the completion of the dropwise addition, the reaction was carried out at −20° C. for 1 hour, and the reaction mixture was poured into water to quench the reaction. The mixture was extracted with dichloromethane, and the organic phases were combined, washed with water, dried, and concentrated to afford a crude compound, which was purified by preparative high performance liquid chromatography to afford the phosphonamide ester racemate (1.4 g). The structure was characterized as follows:

$^1$H NMR (400 MHz, DMSO-$d_6$) δ 8.15-8.12 (m, 2H), 7.34-7.26 (m, 8H), 7.14-7.03 (m, 3H), 5.22-5.12 (m, 1H), 4.39-4.24 (m, 3H), 3.95-3.68 (m, 3H), 3.36-3.28 (m, 1H), 3.05-2.95 (m, 1H), 1.29-1.16 (m, 2H), 1.05-0.95 (m, 3H). ESI-MS (m/z): 497.2 $[M+H]^+$.

Step 3: Preparation of (S)—P—((((R)-1-(6-amino-9H-purin-9-yl)propan-2-yl)oxy)methyl)-phenoxy-N-(2-(benzyloxy)ethyl)-phosphonamide (the Compound of Formula (I)) and (R)—P—((((R)-1-(6-amino-9H-purin-9-yl)propan-2-yl)oxy)methyl)-phenoxy-N-(2-(benzyloxy)ethyl)-phosphonamide (the Compound of Formula (II))

The phosphonamide ester racemate (400 mg) obtained in step 2 was separated by chiral chromatography, and the separation conditions were as follows: separation column CHIRALPAK OD-H 0.46 cm I.D.×15 cm L, mobile phase: hexane/IPA/TEA=70/30/0.1 (V/V/V), flow rate 1.0 ml/min, wavelength UV 254 nm, temperature 35° C. The two title stereoisomeric compounds were isolated.

Isomer (I): (S)—P—(((((R)-1-(6-amino-9H-purin-9-yl)propan-2-yl)oxy)methyl)-phenoxy-N-(2-(benzyloxy)ethyl)-phosphonamide (the Compound of Formula (I))

$R_t$=5.846 min, 198 mg, ee %=98.5%, with its structure being characterized as follows:

$^1$H NMR (400 MHz, DMSO-$d_6$) δ 8.14 (s, 1H), 8.10 (s, 1H), 7.37-7.18 (m, 9H), 7.17-7.10 (m, 1H), 7.05 (dt, J=8.5, 1.2 Hz, 2H), 5.16 (dt, J=11.9, 6.9 Hz, 1H), 4.40 (s, 2H), 4.26 (dd, J=14.4, 3.7 Hz, 1H), 4.14 (dd, J=14.4, 6.6 Hz, 1H), 4.02-3.81 (m, 2H), 3.75 (dd, J=13.5, 9.2 Hz, 1H), 3.28 (d, J=5.7 Hz, 2H), 3.05-2.93 (m, 2H), 1.06 (d, J=6.2 Hz, 3H). ESI-MS (m/z): 497.2 [M+H]$^+$.

Isomer (II): (R)—P—(((((R)-1-(6-amino-9H-purin-9-yl)propan-2-yl)oxy)methyl)-phenoxy-N-(2-(benzyloxy)ethyl)-phosphonamide (the Compound of Formula (II))

R$_t$=7.345 min, 166 mg, ee %=98.3%, with its structure being characterized as follows:
$^1$H NMR (400 MHz, DMSO-d$_6$) δ 8.14 (s, 1H), 8.10 (s, 1H), 7.35-7.21 (m, 9H), 7.13 (t, J=7.3 Hz, 1H), 7.05 (dt, J=8.5, 1.2 Hz, 2H), 5.16 (dt, J=11.8, 6.9 Hz, 1H), 4.40 (s, 2H), 4.26 (dd, J=14.4, 3.7 Hz, 1H), 4.14 (dd, J=14.4, 6.6 Hz, 1H), 3.97-3.81 (m, 2H), 3.75 (dd, J=13.5, 9.2 Hz, 1H), 3.30 (d, J=11.1 Hz, 2H), 3.00 (dq, J=12.5, 6.2 Hz, 2H), 1.06 (d, J=6.2 Hz, 3H). ESI-MS (m/z): 497.2 [M+H]$^+$.

Example 2

Chiral Synthesis of (S)—P—((((R)-1-(6-amino-9H-purin-9-yl)propan-2-yl)oxy)methyl)-phenoxy-N-(2-(benzyloxy)ethyl)-phosphonamide (the Compound of Formula (I))

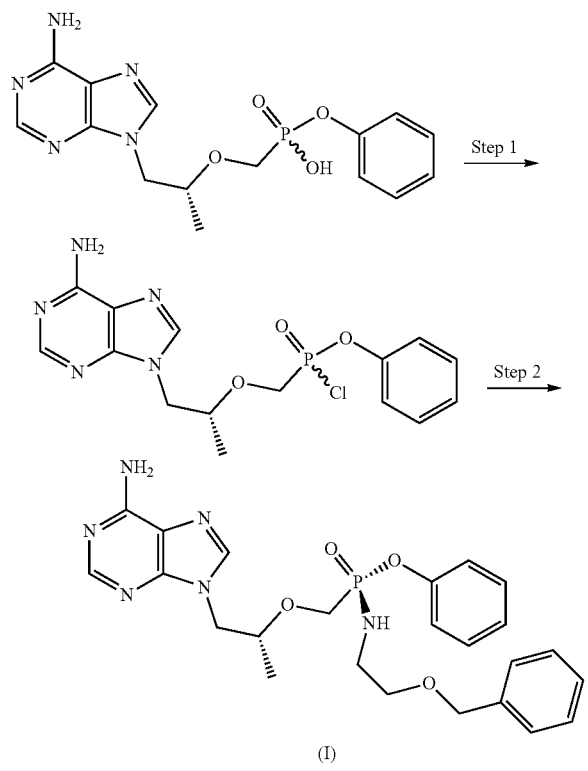

Step 1: Preparation of ((((R)-1-(6-amino-9H-purin-9-yl)-1-methyl-ethoxy)methyl)phenoxyphosphonyl chloride At room temperature, (((1R)-2-(6-amino-9H-purin-9-yl)-1-methylethoxy)methyl)phosphonic acid monophenyl ester (25 g, 68.81 mmol) was dissolved in toluene (250 mL) and thionyl chloride (28.65 g, 240.84 mmol) was added thereto. After the completion of the dropwise addition, the reaction solution was heated to 95° C. and reacted for 48 hours. The reaction solution was distilled under reduced pressure to obtain the title compound (30 g), which was directly used in the subsequent reaction without further purification.
ESI-MS (m/z): 378.1 [M+H]$^+$.

Step 2: Preparation of (2S)-((((1R)-2-(6-amino-9H-purin-9-yl)-1-methyl-ethoxy)methyl-phenoxy-phosphoryl)amino)-3-(2-methylbenzyloxy)-propane 2-(benzyloxy)ethylamine (46.82 g, 309.65 mmol) was dissolved in dry dichloromethane (200 mL) at room temperature, and cooled to −35° C. under nitrogen protection. A solution of the crude product obtained in step 1 (30 g) in toluene (200 mL) was added thereto, with the temperature being controlled to be less than −10° C. After the addition, the reaction was carried out for 1 hour with the temperature maintained at −10° C. A 15% aqueous solution of potassium hydrogen phosphate (400 mL) was added, stirred well, and left to stand for layering. The organic phase was washed sequentially with 15% aqueous solution of potassium hydrogen phosphate (200 mL×2) and deionized water (200 mL×2), and dried. Insoluble material was filtered off, and the filtrate was concentrated to obtain the title compound (30 g). The diastereoisomeric purity was 94.6% as determined by chiral HPLC. The $^1$H NMR data were essentially the same as the $^1$H NMR data for isomer (I) in Example 1.

Example 3

Preparation of an Amorphous Form of the Compound of Formula (I)

About 150 mg of the compound of Formula (I) was weighed and completely dissolved in 4 mL of a good solvent as listed in Table 1 below until the resulting solution was clear. The solution was slowly added dropwise to a glass vial containing 20 mL of distilled water under stirring. After the completion of the dropwise addition, the solution was frozen at a low temperature and lyophilized, and then the solid was collected. The obtained solid was identified as an amorphous form of the compound of Formula (I) by XRPD analysis, and the experimental results are shown in Table 1 below:

TABLE 1

| Solvent | Solid type |
| --- | --- |
| Ethanol/water | Amorphous |
| Acetone/water | Amorphous |

Example 4

Preparation and Characterization of the Crystalline Forms of the Fumarate Salt of the Compound of Formula (I)

Example 4.1. Room Temperature Suspension Stirring Method

Several portions of the fumarate salt of the compound of Formula (I) (15 mg/portion) were weighed and transferred into 5 ml EP tubes, respectively. Then different solvents listed in Table 2 below were added thereto to suspend the fumarate salt. The resulting suspensions were stirred for 8 hours at room temperature, and the solid was collected. If the fumarate salt was completely dissolved to form a clear solution, the 5 ml EP tube containing such a clear solution was placed open at room temperature until the solvent was volatilized completely. The resulting solid were collected and subjected to XRPD analysis, and the results are shown in Table 2 below:

TABLE 2

| Solvent | Collection method | Crystalline form of solid |
| --- | --- | --- |
| Methanol | Natural volatilization | Crystalline form B of the fumarate salt |
| Ethanol | Natural volatilization | Crystalline form A of the fumarate salt |
| Isopropanol | Filtration | Crystalline form A of the fumarate salt |
| N-butanol | Filtration | Crystalline form A of the fumarate salt |
| Isopropyl acetate | Filtration | Crystalline form A of the fumarate salt |
| Isobutyl acetate | Filtration | Crystalline form A of the fumarate salt |
| Dimethyl carbonate | Filtration | Crystalline form A of the fumarate salt |
| Tetrahydrofuran | Natural volatilization | Crystalline form B of the fumarate salt |
| Butanone | Filtration | Crystalline form A of the fumarate salt |
| Isopropyl ether | Filtration | Crystalline form A of the fumarate salt |
| Anisole | Filtration | Crystalline form C of the fumarate salt |
| n-Propanol | Natural volatilization | Crystalline form A of the fumarate salt |

According to Method 4, the molar ratio of the compound of Formula (I) to fumaric acid in the resulting crystalline form of the fumarate salt of the compound of Formula (I) was determined to be 1:1.

The obtained crystals were subjected to XRPD analysis according to Method 1, respectively, to identify three crystalline forms of the fumarate salt, i.e., crystalline forms A, B and C, the XRPD patterns of which are shown in FIGS. 1, 4 and 5, respectively.

Example 4.2. Anti-Solvent Method

Several portions of the fumarate salt of the compound of Formula (I) (40 mg/portion) were weighed, and completely dissolved in ethanol or tetrahydrofuran until the resulting solutions were clear. Then different poor solvents listed in Table 3 below were slowly added dropwise thereto under stirring. Phenomena were observed, and the solid was collected and subjected to XRPD analysis. The results are shown in Table 3 below:

TABLE 3

| Solvent | | Test temperature | Crystalline form of solid |
| --- | --- | --- | --- |
| Good | Poor | | |
| Ethanol | Ethyl acetate | 20~25° C. | Crystalline form A of the fumarate salt |
| | Isopropyl acetate | 20~25° C. | Crystalline form A of the fumarate salt |
| | Petroleum ether | 20~25° C. | Crystalline form A of the fumarate salt |
| | Isopropyl ether | 20~25° C. | Crystalline form A of the fumarate salt |
| | Anisole | 20~25° C. | Crystalline form A of the fumarate salt |
| | Dichloromethane | 20~25° C. | Crystalline form A of the fumarate salt |
| | Acetonitrile | 20~25° C. | Crystalline form A of the fumarate salt |
| | Water | 20~25° C. | Crystalline form A of the fumarate salt |

TABLE 3-continued

| Solvent | | Test temperature | Crystalline form of solid |
| --- | --- | --- | --- |
| Good | Poor | | |
| Tetrahydrofuran | Ethyl acetate | 20~25° C. | Crystalline form A of the fumarate salt |
| | Isopropyl acetate | 20~25° C. | Crystalline form A of the fumarate salt |
| | Isopropyl ether | 20~25° C. | Crystalline form A of the fumarate salt |
| | Anisole | 20~25° C. | Crystalline form A of the fumarate salt |
| | Dichloromethane | 20~25° C. | Crystalline form A of the fumarate salt |
| | Acetonitrile | 20~25° C. | Crystalline form A of the fumarate salt |
| | Water | 20~25° C. | Crystalline form A of the fumarate salt |

The XRPD pattern and DSC graph of the resulting solid are shown in FIGS. 1 and 2, respectively, indicating that all the crystals obtained by the above anti-solvent method was crystalline form A of the fumarate salt of the compound of Formula (I).

Example 4.3. High Temperature Suspension Stirring Method

Several portions of the fumarate salt of the compound of Formula (I) (30 mg/portion) were weighed, transferred separately into 20 ml glass vials, and suspended in different solvents listed in Table 4 below. After stirring at 60° C. for 6 hours, the solid was collected and subjected to XRPD analysis. The results are shown in Table 4 below:

TABLE 4

| Solvent | Collection method | Crystalline form of solid |
| --- | --- | --- |
| Methyl tert-butyl ether | Filtration | Crystalline form A of the fumarate salt |
| Petroleum ether | Filtration | Crystalline form A of the fumarate salt |
| Isopropyl ether | Filtration | Crystalline form A of the fumarate salt |
| Anisole | Filtration | Crystalline form A of the fumarate salt |
| Dichloromethane | Filtration | Crystalline form A of the fumarate salt |
| n-heptane | Filtration | Crystalline form A of the fumarate salt |
| n-hexane | Filtration | Crystalline form A of the fumarate salt |
| Cyclohexane | Filtration | Crystalline form A of the fumarate salt |

The XRPD pattern and DSC graph of the obtained solid were essentially the same as those of the obtained solid in Example 4.2, indicating that all the crystals obtained by the above high temperature suspension stirring method was crystalline form A of the fumarate salt of the compound of Formula (I).

Example 5

Preparation and Characterization of Crystalline Form a of the Fumarate Salt of the Compound of Formula (I)

The free base of the compound of Formula (I) (120 mg) was weighed and placed in a 5 ml EP tube. A 0.1 M fumaric acid solution in methanol (2.4 ml) was added thereto, and the free base was dissolved completely until the solution was clear. The solution was stirred at room temperature for 2 hours, and the solvent was drawn off in vacuum. Half of the sample was placed in an EP tube, to which acetonitrile (1 ml) was added later, and the mixture was stirred overnight at room temperature. The solid was collected after filtration and dried in vacuum for 5 hours.

The sample was subjected to XRPD, TGA/DSC, ¹H-NMR and purity tests.

The XRPD results showed that the crystalline form A of the fumarate salt of the compound of Formula (I) was successfully prepared.

The DSC/TGA analysis graph as illustrated in FIG. 2/3 showed the following: the sample had no weight loss before decomposition; and the sample had no desolvation endothermic peak before the melting point and had a sharp endothermic peak at 125° C. (the onset temperature), indicating the melting point of the sample. By $^1$H-NMR, it was determined that the acid/base molar ratio in the sample was 1, and there was no residual solvent.

The cell parameters of the crystalline form A of the fumarate salt of the compound of Formula (I) are as follows:

Cell Size:
a=13.6818(8) Å
b=6.3963(4) Å
c=17.2967(13) Å
α/°=90
β/°=96.113(6)
γ/°=90
Cell volume: 1505.06 (17) Å$^3$
Crystal system: monoclinic system
Space group: P2$_1$
Number of intramolecular asymmetric units: Z=2.

The crystalline form A of the fumarate salt of the compound of Formula (I) has good crystallinity, a single simple thermal signal (a flat baseline, and a narrow, single and sharp peak in the DSC graph), and a melting point higher than 100° C.

Example 6

Preparation and Characterization of Crystalline Form A of the Citrate Salt of the Compound of Formula (I)

The free base of the compound of Formula (I) (63.4 mg) was weighed and placed in a 5 ml EP tube. A 0.1 M citric acid solution in methanol (1.3 ml) was added thereto, and the free base was dissolved completely until the solution was clear. The solution was stirred at room temperature for 2 hours, and the solvent was drawn off in vacuum. Acetonitrile (1 ml) was added to the EP tube, and the mixture was stirred at room temperature overnight. The solid was collected after filtration and dried in vacuum for 5 hours.

The sample was subjected to XRPD, TGA/DSC, $^1$H-NMR and purity tests.

The XRPD results showed that the crystalline form A of the citrate salt was successfully prepared.

The DSC/TGA analysis graph as illustrated in FIG. 7/8 showed the following: the sample had a weight loss of 7.7% at about 115° C. (the onset temperature) and a broad, sharp endothermic peak at 115° C. (the onset temperature), indicating the melting point of the sample.

The acid/base molar ratio in the sample was determined to be 1 by $^1$H-NMR.

Example 7

Preparation and Characterization of the Crystalline Forms of the Tartrate Salt of the Compound of Formula (I)

The free base of the compound of Formula (I) (300 mg) was weighed and placed in a 20 ml vial. A 0.1 M tartaric acid solution in methanol (6 ml) was added thereto to react for 2 hours at room temperature hermetically, and then the reaction solution was added into EP tubes. The solvent was removed under reduced pressure at 30 C to obtain a white solid, and then the solvents listed in Table 5 below were added thereto, respectively. The solution was allowed to stand for crystallization. Detection by a polarizing microscope (PLM) was carried out after 48 hours, followed by stirring for 48 hours, and the solid was collected and subjected to XRPD analysis. The results are shown in Table 5 below:

TABLE 5

| Solvent | XRPD |
| --- | --- |
| Methanol | A |
| Acetonitrile | A |
| EA | B |
| DCM | A |
| THF | A |
| MTBE | A |
| n-hexane | A |
| Toluene | A |

The obtained crystals were subjected to XRPD analysis according to Method 1, respectively, demonstrating that two crystalline forms of the tartrate, i.e., crystalline forms A and B, were obtained, the XRPD patterns of which are shown in FIGS. 9 and 10, respectively.

Example 8

Preparation and Characterization of Crystalline Form B of the Tartrate Salt of the Compound of Formula (I)

The free base of the compound of Formula (I) (110 mg) was weighed and placed in a 5 ml EP tube. A 0.1 M tartaric acid solution in methanol (2.3 ml) was added thereto, and the free base was dissolved completely until the solution was clear. The solution was stirred at room temperature for 2 hours, and the solvent was drawn off in vacuum. Half of the sample was placed in an EP tube, to which ethyl acetate (1 ml) was added later, and the mixture was stirred overnight at room temperature. The solid was collected after filtration and dried in vacuum for 5 hours.

The sample was subjected to XRPD, TGA/DSC, $^1$H-NMR and purity tests.

The XRPD results showed that crystalline form B of the tartrate salt was successfully prepared.

The DSC/TGA analysis graph as illustrated in FIG. 11/12 showed the following: the sample had no weight loss before decomposition; and the sample had no desolvation endothermic peak before melting point, and had a broad and steady endothermic peak at 120° C. (the onset temperature), and a broad and sharp endothermic peak at 143° C. (the onset temperature), indicating that the sample may be mixed crystals.

The acid/base molar ratio in the sample was determined to be 1 by $^1$H-NMR, and there is no residual solvent.

Example 9

Preparation and Characterization of the Crystalline Forms of the Phosphate of the Compound of Formula (I)

The free base of the compounds of Formula (I) (300 mg) was weighed and placed in a 20 ml vial. A 0.1 M phosphoric acid solution in methanol (6 ml) was added thereto and stirred, and white solid precipitated during stirring. The mixture was stirred at room temperature for 60 minutes, and then subjected to rotary evaporation to dry, thereby obtaining white solid (250 mg). The white solid were added into 10 EP tubes, and then different solvents listed in Table 6 below (1.5 ml each) were added thereto. The mixtures were magnetically stirred for crystallization; and phenomena were continuously observed during the experiment. After detection by a polarizing microscopy (PLM), stirring was continued for 24 hours at room temperature, followed by XRPD analysis. The results are shown in Table 6 below:

TABLE 6

| Solvent | XRPD |
|---|---|
| Methanol | A |
| Acetonitrile | B |
| Acetone | A |
| EA | A |
| DCM | A |
| THF | A |
| Water | B |
| MTBE | B |
| Toluene | B |
| n-hexane | B |

The obtained crystals were subjected to XRPD analysis according to Method 1, respectively, demonstrating that two crystalline forms of the phosphate, i.e., crystalline forms A and B, were obtained, the XRPD patterns of which are shown in FIGS. 13 and 16, respectively.

Example 10

Preparation and Characterization of Crystalline Form A of the Phosphate Salt of the Compound of Formula (I)

The free base of the compounds of Formula (I) (110 mg) was weighed and placed in a 5 ml EP tube. A 0.1 M phosphoric acid solution in methanol (2.2 ml) was added thereto, and the free base was dissolved completely until the solution was clear. The solution was stirred at room temperature for 2 hours, and the solvent was drawn off in vacuum. ⅔ of the sample was placed in an EP tube, to which acetonitrile (1.5 ml) was added later, and the mixture was stirred overnight at room temperature. The solid was collected after filtration and dried in vacuum for 5 hours.

The sample was subjected to XRPD and TGA/DSC analysis.

The XRPD results showed that the crystalline form A of the phosphate salt was successfully prepared.

The DSC/TGA analysis graph as illustrated in FIG. 14/15 showed the following: the sample had a weight loss of 1.9% before 99° C., and had a significant desolvation endothermic peak before the melting point on DSC, and a broad and sharp endothermic peak at 142° C. (the onset temperature), indicating the melting point of the sample.

EXPERIMENTAL EXAMPLES

Experimental Example 1. Physicochemical Properties of Crystalline Form A of the Fumarate Salt of the Compound of Formula (I)

An aqueous solution of pH 2.0 (the pH was adjusted with an appropriate amount of hydrochloric acid), an aqueous solution of pH 7.4 (the pH was adjusted with 10 mM potassium dihydrogen phosphate and an appropriate amount of NaOH), and a fasted-state simulated intestinal fluid (FaSSIF) were prepared as solvents, respectively. Several portions of the sample for test, 1 mg each, were weighed and dissolved in different solvents, 1 mL each. The solutions were thoroughly shaked, and then subjected to ultrasonic operation for 5 minutes. The solutions were observed for whether supersaturation was achieved or not, and if not, the sample was added continuously until supersaturation was achieved. After shaking in a constant temperature shaking water bath for 24 hours, filtration was carried out through a 0.45 uM aqueous filter membrane, followed by HPLC analysis for determination of the solubility. The determination results are shown in Table 7 below:

TABLE 7

| | Solvent | | |
|---|---|---|---|
| Type of crystalline form | $H_2O$ (pH 2.0) | $H_2O$ (pH 7.4) | Fasted-state simulated intestinal fluid (FaSSIF) |
| Crystalline form A of the fumarate salt of the compound of Formula (I) | 1.0 mg/mL | 0.99 mg/mL | 0.91 mg/ml |

As can be seen from the above results, the crystalline form A of the fumarate salt of the compound of Formula (I) of the present invention has had good solubility in both water and the fasted-state intestinal fluid. And after administration, it could be rapidly dissolved in vivo, thereby facilitating the drug absorption.

Experimental Example 2. Hygroscopicity Test

The hygroscopicity of crystalline forms A and B of the fumarate salt was measured by dynamic vapor sorption (DVS) using a DVS Intrinsic (SMS) at 25° C. in a cycle-DMDT mode. The test results are shown in Table 8 below:

TABLE 8

| The hygroscopicity test results of crystalline form A of the fumarate salt for the compound of Formula (I) | |
|---|---|
| Target humidity (%) | Mass change caused by moisture absorption (%) |
| 0 | 0 |
| 10 | 0.019 |
| 20 | 0.04 |
| 30 | 0.057 |
| 40 | 0.078 |
| 50 | 0.096 |
| 60 | 0.117 |
| 70 | 0.137 |
| 80 | 0.158 |
| 90 | 0.192 |

As can be seen from the table above, the crystalline form A of the fumarate salt of the compound of Formula (I) had a mass change (%) of less than 0.2% at a humidity of 80% and 90%, and had little or no hygroscopicity, which is conducive to the storage stability of the prepared drug.

Further, the hygroscopicity result of the crystalline form B of the fumarate salt of the compound of Formula (I) indicated that this crystalline form had a mass change (%) of 0.2% at a humidity of 20%, which is a small change.

Experimental Example 3. Physicochemical Stability Test

An appropriate amount of crystalline form A of the fumarate salt of the compound of Formula (I) of the invention was detected for the physicochemical stability thereof under the following conditions: placed open for 14 days at 40° C./75% RH. XRPD and LC-MS analysis were then carried out to determine the crystalline form and the change in purity. The results showed that the crystal had a relative purity of up to 99% after being placed at 40° C./75% RH for 14 days, without significant change.

Experimental Example 4

Pharmacokinetic Experiment on Crystalline Forms A and C of the Fumarate Salt of the Compound of Formula (I) of the Invention (Having an Acid/Base Molar Ratio of 1:1) in Beagle Dogs The crystalline forms A and C of the fumarate salt of the compound of Formula (I) were encapsulated into capsules and administered intragastrically to beagle dogs at a dose of 2.5 mg/kg. Venous blood was collected at different time points after administration and separately subjected to the detection of the original free base form of the compound of Formula (I) and its metabolite tenofovir (TFV). The test results are shown in Tables 9-10 below:

TABLE 9

In vivo metabolism of crystalline form A of the fumarate salt

| Analyte | | Free base of the compound of Formula (I) | TFV |
| --- | --- | --- | --- |
| $AUC_{INF}$ | h*ng/ml | 66.7 | 923 |
| $AUC_{last}$ | h*ng/ml | 66.2 | 734 |
| $C_{max}$ | ng/ml | 67.4 | 124 |
| $MRT_{INF}$ | h | 1.22 | 13.1 |
| $T_{1/2}$ | h | 0.55 | 9.51 |
| $T_{max}$ | h | 0.69 | 1.25 |

TABLE 10

In vivo metabolism of crystalline form C of the fumarate salt

| Analyte | | Free base of the compound of Formula (I) | TFV |
| --- | --- | --- | --- |
| $AUC_{INF}$ | h*ng/ml | 43.4 | 725 |
| $AUC_{last}$ | h*ng/ml | 41.7 | 564 |
| $C_{max}$ | ng/ml | 77.5 | 122 |
| $MRT_{INF}$ | h | 0.56 | 14.9 |
| $T_{1/2}$ | h | 0.29 | 10.5 |
| $T_{max}$ | h | 0.31 | 1.00 |

As can be seen from Tables 9 and 10, in the Pharmacokinetic experiment in beagle dogs, both the crystalline forms A and C of the fumarate salt of the compound of Formula (I) were rapidly converted to TFV with a half-life of about 10 hours in terms of TFV, and therefore, the administration frequency requirement of quaque die (QD) can be met.

The above specific embodiments describe the present invention in further detail. However, the scope of the above-mentioned subject matter of the present invention should not be construed as being limited to the above examples, and the technical solutions implemented based on the disclosure of the present invention are all within the scope of the present invention.

What is claimed is:

1. Crystalline form A of the fumarate salt of the compound of Formula (I),

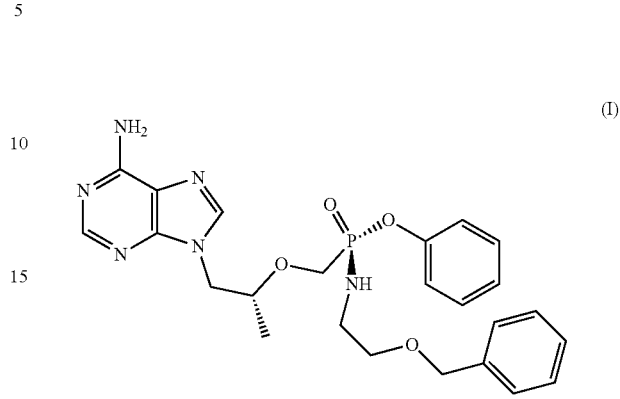

wherein the crystalline form A of the fumarate salt of the compound of Formula (I) has an XRPD pattern comprising characteristic peaks at diffraction angles (2θ) of 5.1±0.2°, 6.4±0.2°, 16.3±0.2°, 18.7±0.2°, and 28.2±0.2°.

2. A method for preparing the crystalline form A of the fumarate salt of the compound of Formula (I) according to claim 1, comprising:

suspending the fumarate salt of the compound of Formula (I) in a solvent selected from the group consisting of ethanol, isopropanol, n-butanol, isopropyl acetate, isobutyl acetate, dimethyl carbonate, butanone, isopropyl ether, and propanol, stirring the resulting suspension for 8 hours at room temperature, and collecting the resulting solid; or completely dissolving the fumarate salt of the compound of Formula (I) in ethanol until the resulting solution is clear, slowly adding dropwise a poor solvent selected from the group consisting of ethyl acetate, isopropyl acetate, petroleum ether, isopropyl ether, anisole, dichloromethane, acetonitrile and water at 20~25° C., and collecting the resulting solid; or completely dissolving the fumarate salt of the compound of Formula (I) in tetrahydrofuran until the resulting solution is clear, slowly adding dropwise a poor solvent selected from the group consisting of ethyl acetate, isopropyl acetate, isopropyl ether, anisole, dichloromethane, acetonitrile and water at 20~25° C., and collecting the resulting solid; or suspending the fumarate salt of the compound of Formula (I) in a solvent selected from the group consisting of methyl tert-butyl ether, petroleum ether, isopropyl ether, anisole, dichloromethane, n-heptane, n-hexane and cyclohexane, stirring at 60° C. for 6 hours, and collecting the resulting solid; or completely dissolving the free base of the compound of Formula (I) with a 0.1 M fumaric acid solution in methanol until the resulting solution is clear, stirring at room temperature for 2 hours, removing the solvent, adding acetonitrile, stirring overnight at room temperature, and collecting the resulting solid.

3. Crystalline form B of the fumarate salt of the compound of Formula (I),

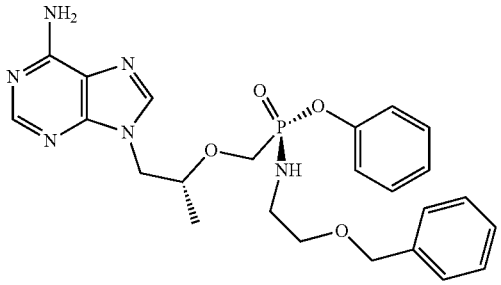

wherein
the crystalline form B of the fumarate salt of the compound of Formula (I) has an XRPD pattern comprising characteristic peaks at diffraction angles (2θ) of 10.2±0.2°, 10.8±0.2°, 17.1±0.2°, 18.8±0.2°, and 21.7±0.2°.

4. A method for preparing the crystalline form B of the fumarate salt of the compound of Formula (I) according to claim 3, comprising:
suspending the fumarate salt of the compound of Formula (I) in methanol or tetrahydrofuran, stirring the resulting suspension for 8 hours at room temperature, and collecting the resulting solid.

5. Crystalline form C of the fumarate salt of the compound of Formula (I),

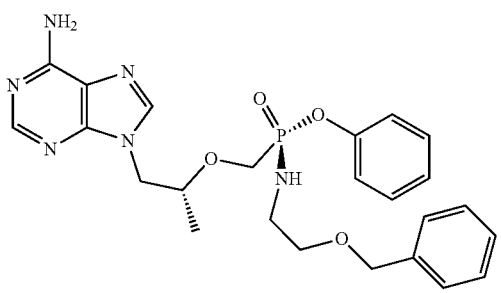

wherein
the crystalline form C of the fumarate salt of the compound of Formula (I) has an XRPD pattern comprising characteristic peaks at diffraction angles (2θ) of 4.3±0.2°, 6.8±0.2°, 14.3±0.2°, 18.8±0.2°, and 27.9±0.2°.

6. A method for preparing the crystalline form C of the fumarate salt of the compound of Formula (I) according to claim 5, comprising:
suspending the fumarate salt of the compound of Formula (I) in anisole, stirring the resulting suspension for 8 hours at room temperature, and collecting the resulting solid.

7. A method for prophylaxis or treating viral infectious diseases, comprising administering to a subject in need thereof the crystalline form A of the fumarate salt of the compound of Formula (I) according to claim 1.

8. A method for prophylaxis or treating viral infectious diseases, comprising administering to a subject in need thereof the crystalline form B of the fumarate salt of the compound of Formula (I) according to claim 3.

9. A method for prophylaxis or treating viral infectious diseases, comprising administering to a subject in need thereof the crystalline form C of the fumarate salt of the compound of Formula (I) according to claim 5.

10. A pharmaceutical composition, comprising:
i) the crystalline form A of the fumarate salt of the compound of Formula (I) according to claim 1; and
ii) one or more pharmaceutically acceptable carriers.

11. A pharmaceutical composition, comprising:
i) the crystalline form B of the fumarate salt of the compound of Formula (I) according to claim 3; and
ii) one or more pharmaceutically acceptable carriers.

12. A pharmaceutical composition, comprising:
i) the crystalline form C of the fumarate salt of the compound of Formula (I) according to claim 5; and
ii) one or more pharmaceutically acceptable carriers.

13. The crystalline form A of the fumarate salt of the compound of Formula (I) according to claim 1, wherein the crystalline form A of the fumarate salt of the compound of Formula (I) has an XRPD pattern comprising characteristic peaks at diffraction angles (2θ) of 5.1±0.2°, 6.4±0.2°, 14.7±0.2°, 15.3±0.2°, 16.3±0.2°, 18.0±0.2°, 18.7±0.2°, 19.2±0.2°, 28.2±0.2°, and 29.6±0.2°.

14. The crystalline form A of the fumarate salt of the compound of Formula (I) according to claim 13, wherein the crystalline form A of the fumarate salt of the compound of Formula (I) has an XRPD pattern comprising characteristic peaks at diffraction angles (2θ) of 5.1±0.2, 6.4±0.2°, 12.9±0.2°, 14.7±0.2°, 15.3±0.2°, 16.3±0.2°, 18.0±0.2°, 18.7±0.2°, 18.9±0.2°, 19.2±0.2°, 20.0±0.2°, 20.7±0.2°, 22.2±0.2°, 24.0±0.2°, 24.9±0.2°, 25.3±0.2°, 27.8±0.2°, 28.2±0.2°, and 29.6±0.2°.

15. The crystalline form A of the fumarate salt of the compound of Formula (I) according to claim 14, wherein the crystalline form A of the fumarate salt of the compound of Formula (I) has an XRPD pattern comprising characteristic peaks as shown in FIG. 1.

16. The crystalline form A of the fumarate salt of the compound of Formula (I) according to claim 15, wherein the crystalline form A of the fumarate salt of the compound of Formula (I) has the following cell parameters:
Cell size:
a=13.6818(8) Å
b=6.3963(4) Å
c=17.2967(13) Å
α/°=90
β/°=96.113(6)
γ/°=90
Cell volume: 1505.06 (17) Å$^3$
Crystal system: monoclinic system
Space group: P2$_1$
Number of intramolecular asymmetric units: Z=2.

17. The crystalline form B of the fumarate salt of the compound of Formula (I) according to claim 3, wherein the crystalline form B of the fumarate salt of the compound of Formula (I) has an XRPD pattern comprising characteristic peaks at diffraction angles (2θ) of 9.7±0.2°, 10.2±0.2°, 10.8±0.2°, 14.7±0.2°, 17.1±0.2°, 18.1±0.2°, 18.8±0.2°, 19.2±0.2°, 20.6±0.2°, and 21.7±0.2°.

18. The crystalline form B of the fumarate salt of the compound of Formula (I) according to claim 17, wherein the crystalline form B of the fumarate salt of the compound of Formula (I) has an XRPD pattern comprising characteristic peaks at diffraction angles (2θ) of 9.7±0.2°, 10.2±0.2°, 10.8±0.2°, 11.8±0.2°, 13.2±0.2°, 13.8±0.2°, 14.7±0.2°, 16.1±0.2°, 17.1±0.2°, 18.1±0.2°, 18.8±0.2°, 19.2±0.2, 20.6±0.2°, 21.7±0.2°, 22.3±0.2°, 23.8±0.2°, 26.7±0.2°, 27.0±0.2°, 27.5±0.2°, and 29.3±0.2°.

19. The crystalline form B of the fumarate salt of the compound of Formula (I) according to claim 18, wherein the crystalline form B of the fumarate salt of the compound of Formula (I) has an XRPD pattern comprising characteristic peaks as shown in FIG. 4.

20. The crystalline form C of the fumarate salt of the compound of Formula (I) according to claim 5, wherein the crystalline form C of the fumarate salt of the compound of Formula (I) has an XRPD pattern comprising characteristic peaks at diffraction angles (2θ) of 4.3±0.2°, 6.6±0.2°, 6.8±0.2°, 14.3±0.2°, 16.6±0.2°, 18.5±0.2°, 18.8±0.2°, 19.2±0.2°, 27.6±0.2°, and 27.9±0.2°.

21. The crystalline form C of the fumarate salt of the compound of Formula (I) according to claim 20, wherein the crystalline form C of the fumarate salt of the compound of Formula (I) has an XRPD pattern comprising characteristic peaks at diffraction angles (2θ) of 4.3±0.2°, 6.6±0.2°, 6.8±0.2°, 13.0±0.2°, 14.3±0.2°, 15.3±0.2°, 15.8±0.2°, 16.2±0.2°, 16.6±0.2°, 17.3±0.2°, 18.5±0.2°, 18.8±0.2°, 19.2±0.2°, 20.1±0.2°, 22.6±0.2°, 23.3±0.2°, 25.8±0.2°, 26.2±0.2°, 27.6±0.2°, and 27.9±0.2°.

22. The crystalline form C of the fumarate salt of the compound of Formula (I) according to claim 21, wherein the crystalline form C of the fumarate salt of the compound of Formula (I) has an XRPD pattern comprising characteristic peaks as shown in FIG. 5.

23. The method according to claim 7, wherein the viral infectious disease is hepatitis B.

24. The method according to claim 8, wherein the viral infectious disease is hepatitis B.

25. The method according to claim 9, wherein the viral infectious disease is hepatitis B.

* * * * *